(12) United States Patent
Bartsch et al.

(10) Patent No.: US 7,015,190 B1
(45) Date of Patent: Mar. 21, 2006

(54) METHOD FOR ENHANCING LONG-TERM MEMORY IN A SUBJECT AND USES THEREOF

(75) Inventors: Dusan Bartsch, New York, NY (US); Eric R. Kandel, Riverdale, NY (US); Mirella Ghirardi, Turin (IT)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/656,811

(22) Filed: Jun. 3, 1996

(51) Int. Cl.
*A61K 38/00* (2006.01)
*A61K 48/00* (2006.01)

(52) U.S. Cl. .......................... 514/2; 514/44
(58) Field of Classification Search ............ 424/130.1; 514/2, 44
See application file for complete search history.

(56) References Cited

FOREIGN PATENT DOCUMENTS

WO    WO 96/11270 A    4/1996

OTHER PUBLICATIONS

Glanzman Trends in Neuroscience (Jan. 1995) 18(1) pp. 30-36.*
Cooper et al "The Biochemical Basis of Neuropharmacology" 6st Edition (1991) Oxford University Press, Inc USA.*
Alberini, C. et al. (1994) C/EBP is an immediate-early gene required for the consolidation of long-term facilitation in Aplysia. Cell. 76:1099-1114 (Exhibit 2).
Bailey, C.H. & Kandel, E.R. (1993) Structural changes accompanying memory storage. *Annu. Rev. Physiol.* 55:397-426 (Exhibit 3).
Bartsch, Dusan et al. (1995) Alysia CREB2 Represses Long-term Facilitation: Relief of Repression Converts Transient Facilitation into Long-term Functional and Structural Change. Cell. 83:979-992 (Exhibit 4).
Bourtchuladze, R. et al. (1994) Deficient long-term memory in mice with a targeted mutation of the cAMP responsive element-binding protein. Cell. 79:59-68 (Exhibit 5).
Dash, P.K. et al. (1990) Injection of the cAMP-responsive element into the nucleus of Aplysia sensory neurons blocks long-term facilitation. *Nature.* 345:718-721 (Exhibit 6).
Karpinski, B.A. et al. (1992) Molecular cloning of human CREB-2: An ATF/CREB trasncription factor that can negatively regulate transcription from the cAMP response element. Proc. Natl. Acad. Sci. USA. 89:4820-4824 (Exhibit 7).
Lemaigre, F.P. et al (1993) The cAMP response element binding protein, CREB, is a potent inhibitor of diverse transcriptional activators. Nucleic Acids Res. 21:2907-2911 (Exhibit 8).
Yin, J.C.P. et al. (1995) CREB as a Memory Modulator: Induced Expression of a dCREB2 Activator Isoform Enhances Long-term Memory in Drosophila. Cell. 81:107-115 (Exhibit 9).
Yin, J.C.P. et al. (1994) Induction of a Dominant Negative CREB Transgene Specifically Blocks Long-term Memory in Drosophila. *Cell.* 79:49-58 (Exhibit 10).
Bartsch, D. et al. (1995), "Aplysia CREB2 Represses Long-Term Facilitation: Relief of Repression Converts Transient Facilitation into Long-Term Functional . . . ", Cell 83:979-992.
European Search report issued Jan. 28, 2005 in connection with European Patent Application No. 979268962, (do not publish).

* cited by examiner

*Primary Examiner*—Michael Pak
(74) *Attorney, Agent, or Firm*—John P. White, Esq.; Cooper & Dunham LLP

(57) ABSTRACT

The present invention provides for a method to enhance long-term memory in a subject whose cAMP-responsive gene expression is repressed due to binding of a cAMP-response-element-binding-protein-2 to a protein or a DNA associated with cAMP-responsive gene expression, or both, which comprises administering to the subject a compound capable of interfering with such binding in an amount effective to interfere with binding of the protein or the DNA so as to thereby derepress cAMP-responsive gene expression in the subject and enhance the subject's long-term memory.

5 Claims, 14 Drawing Sheets

FIG. 1A

```
  1 MELDLWSEDFQLAREWGLEMPVVQTDGQFGDLKSTSRHGG
 41 DESLSLQPQGATLKLEPFEEDVLGAEWMESSDGSFLDA    II
 81 GDNHERHPFFESNLEFTSLTEDDSTSKDILSSTLQFP
121 TOPVNIPLYASHGAEDFSAETEFENHLSPPDSPEQVAPVI
161 NLEPVELTASHMTVISPDGLLGGMELASESLTFTELDFVN
201 FNDSAVGSIGGAEELLGSPLSVDDVESTISFSGPSSPETS
241 QSSIESSPELYKVISTSIDASKRFSPYSRSKSKQSVK
281 TSDAKAPRKTRTPAQPVPEHVIMEHLDKKRKKLQNKNAA    I
321 IRYRMKKGEAQGIKGEEQEELNTKLKTKVDDLQREIK
361 YKNLMEDVCKAKGIQLK
```

FIG. 1B

```
306 LDKKDRKKLQNKNAAIRYRMKKGEAQGIKGEEQELEE    ApCREB-2
308 LDKKLKKMEQNKTAATEEVRAEQEALTGECKELEK     mATF-4
278 LDKKLKKMEQNKTAATRRQKRMKKGEALTGECKELEK    hCREB-2

344 LNTKLKTKVDDLQREIKAAEIQLKGIQLK           ApCREB-2
346 KNEALKEKADSLAKEIQYLKKARGKKRVP           mATF-4
316 KNEALKERADSLAKEIQYLKKARGKKRVP           hCREB-2
```

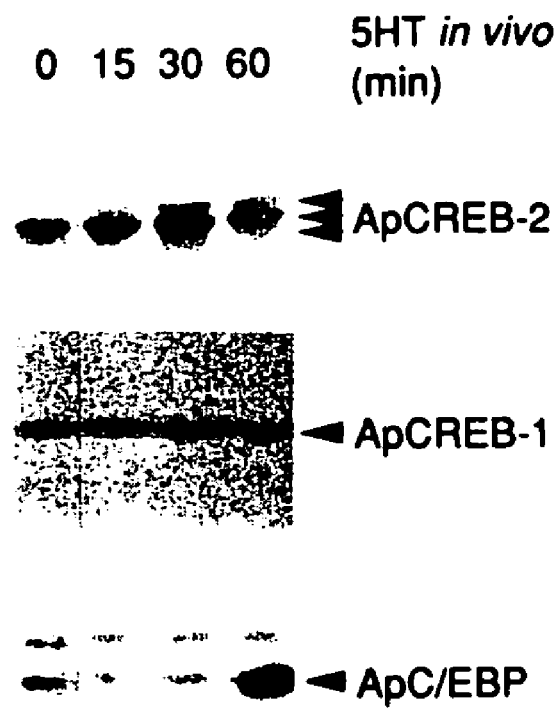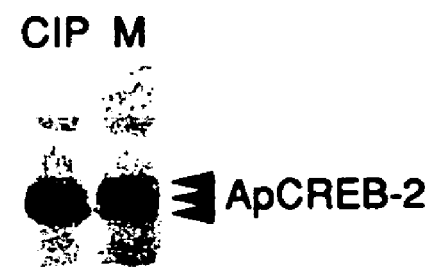
FIG. 4A
FIG. 4B

FIG. 6A

```
CRE                TGACGTCA
BS1 - ApCREB - 2   AGTATTGCGTCATC
BS2 - ApC/EBP      ACTATTGCGCAATC
```

FIG. 10A 0 hr

FIG. 10B 24 hrs

CREB-2 Ab
1 x 5HT

Control
1 x 5HT

METHOD FOR ENHANCING LONG-TERM MEMORY IN A SUBJECT AND USES THEREOF

The invention disclosed herein was made with Government support under Grants No. MH37134 and GM32099 from NIH. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

INTRODUCTION

Memory acquisition has at least two components, a transient short-term memory lasting minutes to hours that can be followed by a more persistent and self-maintained long-term memory lasting days to years. Whereas short-term memory requires only covalent modifications of preexisting proteins, long-term memory requires the synthesis of new mRNA and proteins (Flexner et al., 1963; Davis and Squire, 1984; Montarolo et al., 1986;) and is accompanied by the growth of new synaptic connections (Bailey and Kandel, 1993).

The switch from short- to long-term memory can be studied on the molecular level in the gill-withdrawal reflex of the marine snail *Aplysia*. Following a single noxious stimulus to the tail, the animal acquires a short-term memory for the noxious stimulus lasting minutes, during which time both the amplitude and the duration of the gill-withdrawal reflex to tactile stimulation of the siphon is greatly enhanced (Pinsker et al., 1970; Carew et al., 1971). Following five or more spaced sensitizing stimuli, the animal acquires a long-term memory lasting days or weeks (Carew et al., 1972; Pinsker et al., 1973). The short-term memory does not require new protein synthesis, whereas long-term memory is blocked by inhibitors of protein and RNA synthesis (Montarolo et al., 1986; Castellucci et al., 1989; Bailey et al., 1992).

A cellular representation of both types of memeory storage can be studied in cocultures of a single sensory neuron and a single motor neuron of the gill withdrawal reflex. Here one brief application of 5-HT, a modulatory transmitter released in vivo by interneurons activated by sensitizing tail stimuli, produces short-term facilitation that results from a strengthening of preexisting synaptic connections between the sensory and motor cell by means of covalent modifications of preexisting proteins (Montarolo et al., 1986; Rayport and Schacher, 1986). By contrast, five applications of 5-HT, spaced by 20 min, produce long-term facilitation that lasts for more than one day, is dependent on the synthesis of mRNA and protein, and is accompanied by an increase in the number of sensory neuron synaptic terminal varicosities in contact with the motor neuron (Montarolo et al., 1986; Glanzman et al., 1990; Bailey et al., 1992).

SUMMARY OF THE INVENTION

The present invention provides for a method to enhance long-term memory in a subject whose cAMP-responsive gene expression is repressed due to binding of a cAMP-response-element-binding-protein-2 to a protein or a DNA associated with cAMP-responsive gene expression, or both, which comprises administering to the subject a compound capable of interfering with such binding in an amount effective to interfere with binding of the protein or the DNA so as to thereby derepress cAMP-responsive gene expression in the subject and enhance the subject's long-term memory.

BRIEF DESCRIPTION OF THE FIGURES

FIGS. 1A and 1B. Amino Acid Sequence of ApCREB-2.

(A) The predicted amino acid sequence of ApCREB-2 deduced from two independent clones isolated by a yeast two-hybrid screen of an *Aplysia* CNS cDNA library. The bZIP domain that interacts with ApC/EBP is boxed and labeled I. Within this domain, hydrophobic residues of the leucine zipper motif are shaded. The box labeled II delineates a second leucine heptad repeat. ApCREB-2 contains a consensus sequence for PKC phosphorylation (aa 271–274, bold, underlined). In addition, ApCREB-2 has putative consensus sequences for MAP kinase in similar positions to those in human CREB-2 and mouse ATF-4 (aa 235–238 and aa 150–153, italics, underlined). (SEQ ID NO 1) This sequence and ApCREB-2 cDNA sequence were deposited in GenBank. See deposit information hereinbelow.

(FIG. 1B) The C-terminal 79 amino acids of ApCREB-2 containing the bZIP domain aligned with the bZIP domains of mouse ATF-4 (mATF-4) and human CREB-2 (hCREB-2). The numbers on the left margin refer to the adjacent amino acids, and an asterisk marks the hydrophobic residues of the leucine zippers. Identical residues are boxed. Within the bZIP region the compared proteins are 50% identical. A cysteine residue in the basic region conserved in most bZIP proteins is substituted for a tyrosine at position 323 (shaded). This substitution, as well as the tyrosine at position 361 (shaded) within the leucine zipper, is conserved among all three proteins: ApCREB-2, hCREB-2 and mATF-4. (SEQ ID NO 2)

Figure 2A:
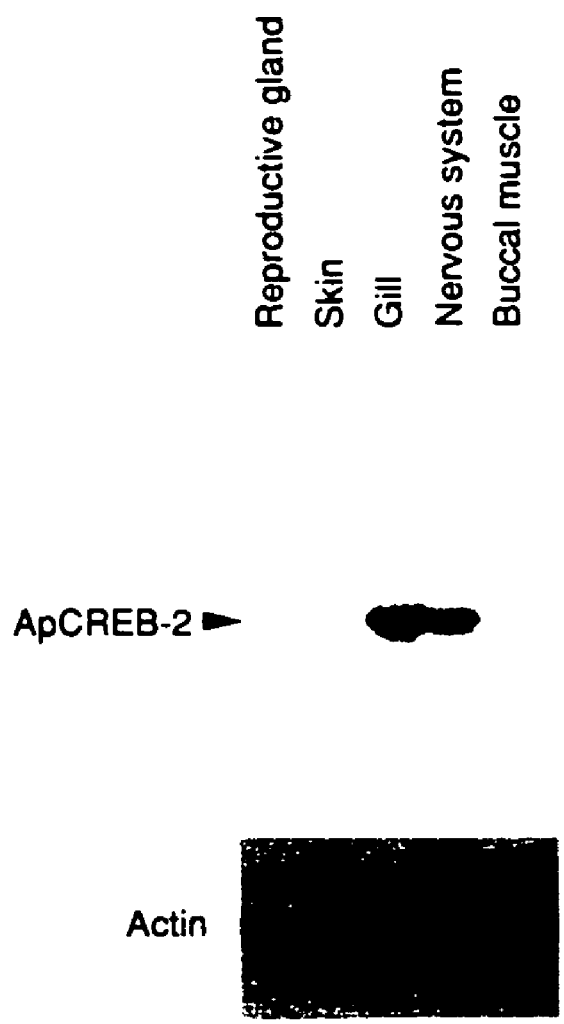
Figure 2B:
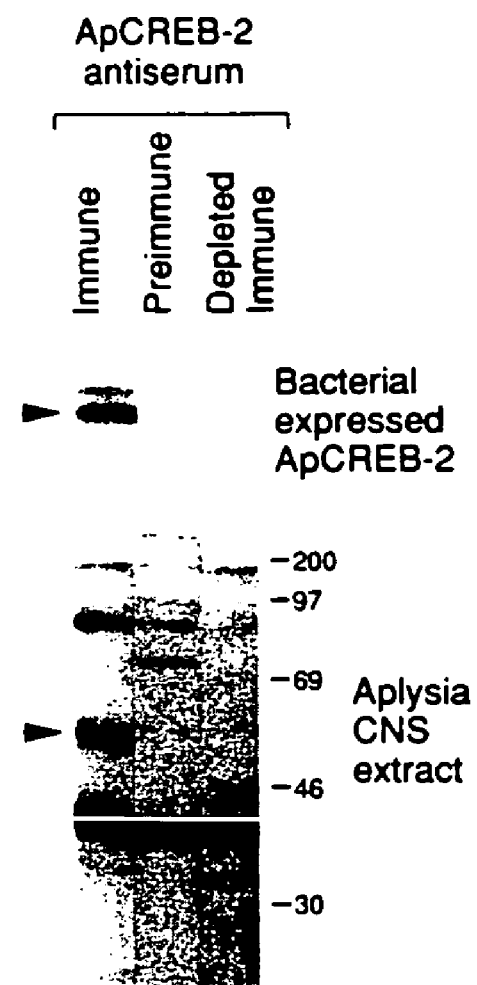
Figure 2C:
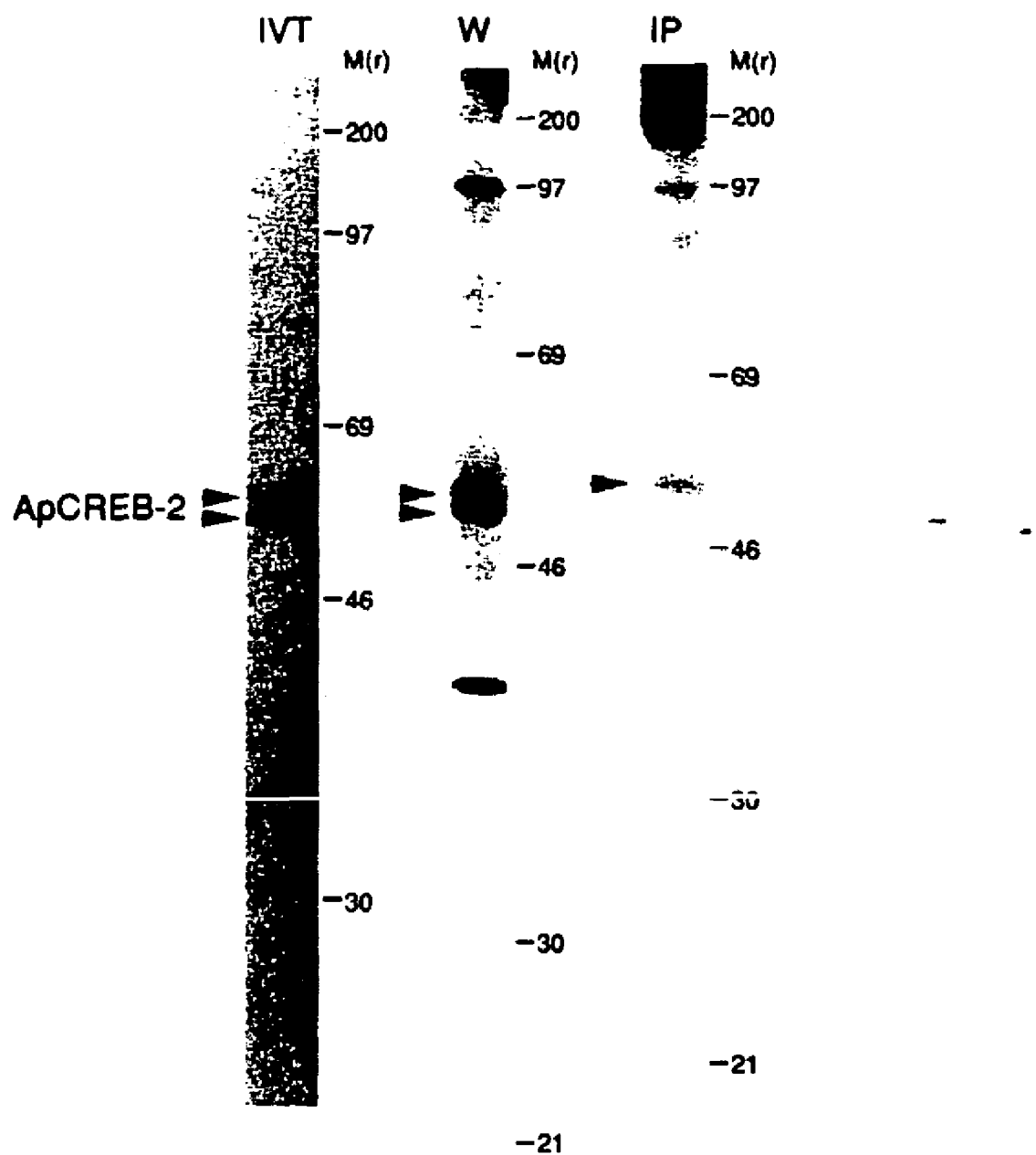

FIGS. 2A, 2B and 2C. Expression of ApCREB-2 in *Aplysia* Tissues.

(FIG. 2A) Northern blot analysis of ApCREB-2 mRNA expression. The tissue used as the source of RNA is indicated above each lane. Five $\mu$g of total RNA was loaded in each lane. The arrowhead indicates the position of ApCREB-2 mRNA detected by hybridization with a full length ApCREB-2 cDNA probe (upper panel) and *Aplysia* actin cDNA probe (lower panel). ApCREB-2 mRNA is highly expressed in central nervous system (CNS) and gill.

(FIG. 2B) Western blot analysis of bacterial-expressed recombinant ApCREB-2 (upper panel) and Aplysia CNS protein extract (lower panel). 2 µg of recombinant ApCREB-2 or 15 µg of total protein isolated from Aplysia CNS were separated by SDS-PAGE, electroblotted, and probed with antiserum raised against recombinant ApCREB-2 (immune), preimmune serum and immune ApCREB-2 antiserum preincubated with immobilized immunizing ApCREB-2 antigen (depleted immune). Multiple bands recognized by the anti-ApCREB-2 antibodies, indicated by arrowhead, are specifically blocked by depleting the immune serum with recombinant ApCREB-2. Positions of molecular mass markers in kD are indicated.

(FIG. 2C) Analysis of ApCREB-2 protein expression in Aplysia CNS using affinity-purified antibodies. The specific ApCREB-2 signals are indicated by arrowheads. (IVT) $^{35}$S-methionine labeled ApCREB-2 protein in vitro translated in rabbit reticulocyte lysate, separated by SDS-PAGE and visualized by fluorography. (W) Western blot of Aplysia CNS protein extract from animals exposed to 5-HT in vivo for 2 hr. 20 µg of total CNS extract were subjected to SDS-PAGE, electroblotted, and probed with affinity-purified anti-ApCREB-2 antibodies. (IP) Immunoprecipitation, using affinity purified anti-ApCREB-2 antibodies, from total Aplysia CNS dissected from anesthetized animals and metabolically labeled with $^{35}$S-methionine.

ApCREB-2 is expressed in the Aplysia central nervous system and migrates on SDS-PAGE as multiple bands with an apparent molecular weight of around 50 kD.

Figure 3A:
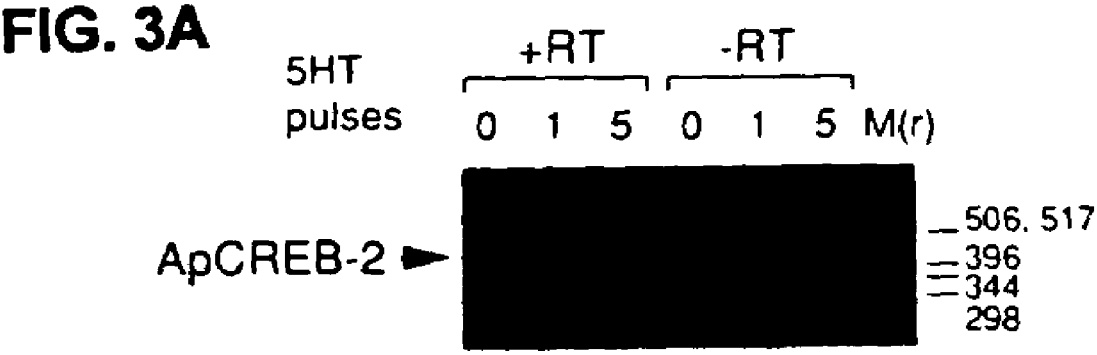
Figure 3B:

FIGS. 3A and 3B. ApCREB-2 is Constitutively Expressed in the Sensory Neurons of Aplysia.

(FIG. 3A) A 450 bp of ApCREB-2 cDNA amplified by RT-PCR from Aplysia sensory neurons. RNA was isolated from cultures of approximately 200 Aplysia sensory neurons that had been exposed to none, one, or five pulses of 5-HT (10 µM) as indicated. As a control, one half of the RNA was processed omitting reverse transcriptase from the reaction (—RT). ApCREB-2 RNA is constitutively expressed in Aplysia sensory neurons.

(FIG. 3B) Northern blot analysis of RNA isolated from CNS of Aplysia exposed to 5-HT in vivo. CNSs were dissected from anesthetized animals after exposing them in vivo to 5-HT (50 µM) for the time indicated above each lane. Eight µg of total RNA from each timepoint was separated in a 1% agarose gel, blotted and consecutively hybridized with probes specific for ApCREB-2, ApCREB-1, ApC/EBP, and ribosomal protein S4 transcripts.

Unlike ApC/EBP mRNA, ApCREB-2 and ApCREB-1 mRNAs are constitutively expressed in the Aplysia central nervous system, and their steady-state level is not affected by exposure to 5-HT in vivo.

FIGS. 4A and 4B. ApCREB-2 Is a Phosphoprotein In Vivo.

(FIG. 4A) Western blot of Aplysia CNS extracts from animals exposed to 5-HT in vivo for the time indicated above each lane. The blots were probed with anti-ApCREB-2, anti-rat CREB-1, and anti-ApC/EBP antibodies. The positions of these proteins are indicated by arrowheads. ApCREB-2 migrates as multiple bands. Note the appearance of a slower migrating ApCREB-2 specific signal in the course of 5-HT exposure.

(FIG. 4B) Western blot of Aplysia CNS extract from animals exposed to 5-HT in vivo for 90 min and incubated with phosphatase (CIP) or mock treated (M). The positions of ApCREB-2 specific signals are indicated by arrows. Note the appearance of a faster migrating ApCREB-2 in SDS-PAGE after hosphatase treatment. These data indicate that ApCREB-2 is a phosphoprotein in vivo and that the phosphorylation level of ApCREB-2 changes following exposure to 5-HT.

Figure 5B:
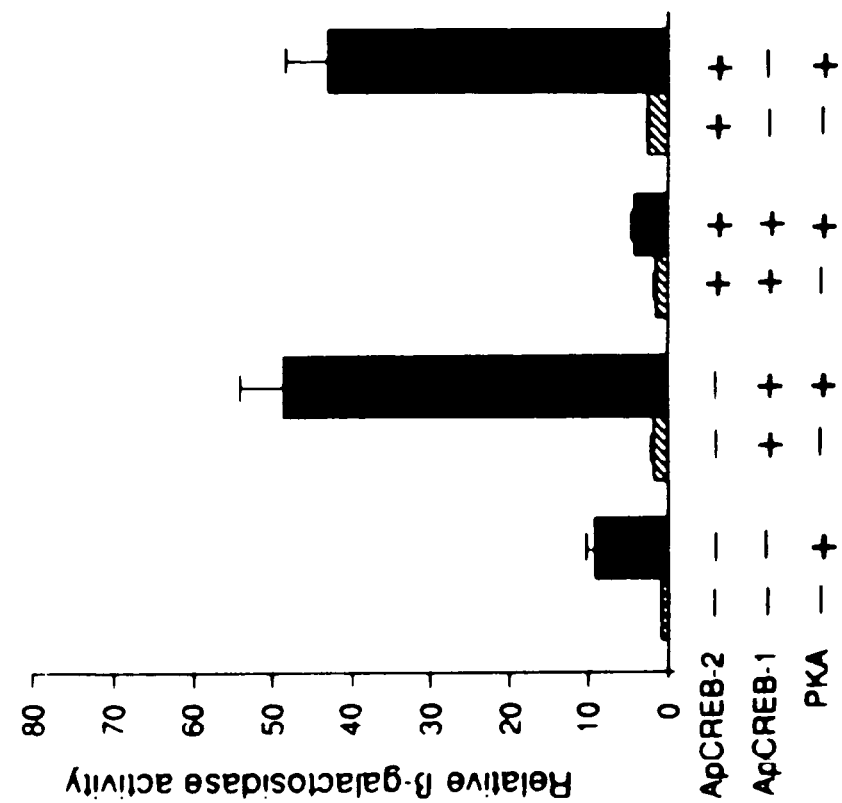
Figure 5A:
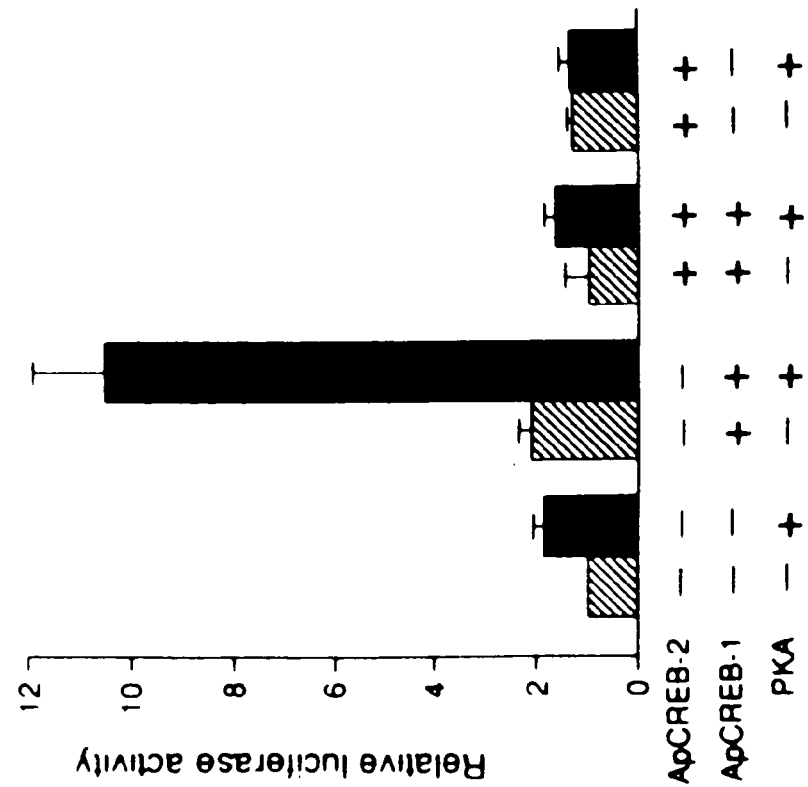

FIGS. 5A and 5B. Effect of ApCREB-2 and ApCREB-1 Expression on CRE-Mediated Transcription in F9 Cells.

(FIG. 5A) Mouse F9 cells were transiently cotransfected with 1 µg of pGL3-CRE reporter plasmid along with 1 µg of each of the indicated expression plasmids: ApCREB-2=pR-cRSV-ApCREB-2, ApCREB-1=pRcRSV-ApCREB-1, PKA=pRcRSV-PKA. All transfections were adjusted to 4 µg total DNA with pRcRSV vector DNA. The luciferase activity of the reporter was normalized to (-galactosidase activity from 0.2 µg of the cotransfected RSV-lacZ expression plasmid. The relative luciferase activity was calculated by comparing the activities measured in cotransfection experiments to the activity of pGL3-CRE alone (arbitrarily set at 1.0). Each bar represents the mean of at least nine independent transfections ±SEM. ApCREB-2 does not activate transcription on its own, but represses the activation mediated by ApCREB-1 on a minimal CRE control region.

(FIG. 5B) Transient transfections of F9 cells using a 5xCRE-VIP-lacZ reporter plasmid. The indicated expression constructs were cotransfected with 5xCRE-VIP-lacZ reporter as in (A), except that relative (-galactosidase activity was calculated relative to 5xCRE-VIP-lacZ reporter and normalized to the luciferase activity of cotransfected pRSV-luc. ApCREB-2 and ApCREB-1 are activators of 5xCRE-VIP-lacZ reporter, but become mutual repressors when coexpressed.

Figure 6B:
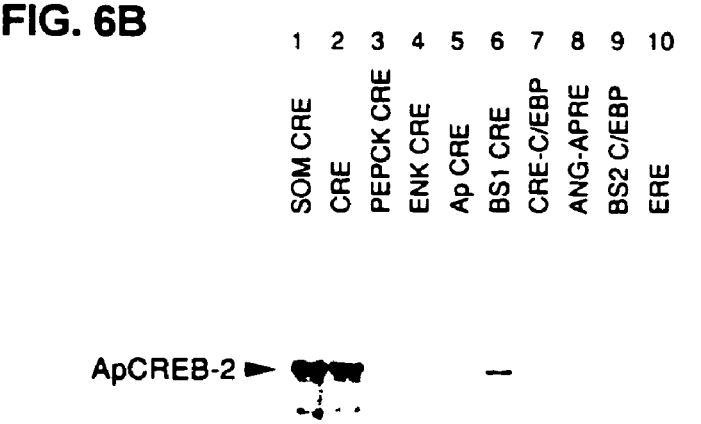
Figure 6C:
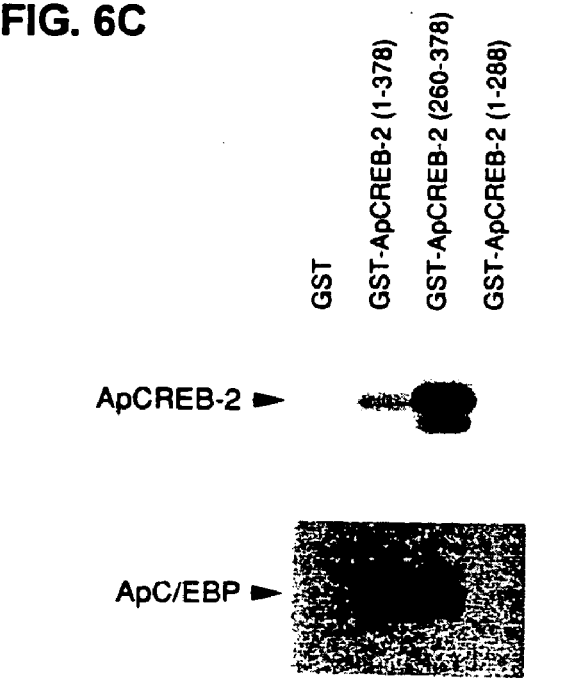

FIGS. 6A, 6B and 6C. ApCREB-2 Homodimers Bind to CRE (Seq ID No 3).

(FIG. 6A) The sequence of DNA binding sites for ApCREB-2 (BS1) and ApC/EBP (BS2). Optimal DNA binding sequences were selected from a pool of double-stranded random twentymers by repeated binding and PCR amplification. In both BS1 (Seq ID No 4) and BS2 (Seq ID No 5), the homology to the CAAT box is underlined and the homology to the palindromic CRE site (above) is bold.

(FIG. 6B) Specificity of recombinant 6His-ApCREB-2 binding to symmetrical and asymmetrical CREs and CAAT binding sequences. Electrophoretic mobility shift assay with double-stranded oligonucleotides containing the CREs of the somatostatin gene (1) and its core palindrome (2), PEPCK gene (3), proenkephalin gene (4) and putative CRE of the ApC/EBP gene (5). Also tested were the BS1 selected ApCREB-2 DNA-binding sequence (6), a composite CRE-CAAT binding site (7), the C/EBP-binding APRE of the angiotensin gene (8), the selected BS2 ApC/EBP DNA-binding site (9), and the C/EBP-binding ERE of the fos promoter (10). The arrowhead indicates the position of a specific ApCREB-2 shift and an asterisk marks the unbound oligonucleotide probes. The specificities of the shifts were confirmed by competition with 10 and 100 molar excess of nonradioactive oligonucleotides and mutants of the CRE and C/EBP sites (not shown). Recombinant ApCREB-2 binds directly to the high-affinity somatostatin CRE as well as to BS1 and the CRE from the proenkephalin gene, but does not bind to any of the CAAT sites tested.

(FIG. 6C) Interaction of in vitro translated ApCREB-2 and ApC/EBP with bacterial-expressed glutathione S-transferase (GST) fusions of ApCREB-2. Glutathione-agarose beads saturated with equal amounts of bacterial-expressed GST-ApCREB-2 and its deletion mutants (indicated above lanes) were incubated with $^{35}$S-labeled ApCREB-2 or ApC/EBP proteins, washed, and eluted bound proteins resolved by SDS-PAGE. ApCREB-2 forms weak homodimers, but that homodimer formation can be greatly increased by deleting the N-terminal 260 amino acids which contain the second leucine zipper.

FIGS. 7A, 7B, 7C and 7D. Time Course of the Effect of Injection of ApCREB-2 antiserum on Short- and Long-Term Facilitation.

(FIG. 7A) Time course of EPSP amplitude changes recorded in motor neuron L7 in response to stimulation of the sensory neuron (expressed as percent change in the amplitude of the EPSP) after single and multiple applications of 5-HT to Aplysia sensory-motor neuron cocultures. Changes in EPSP amplitude after application of one 5 min pulse of 5-HT (1×5-HT, short-term facilitation) and one 5 min pulse of 5-HT paired with injection of anti-ApCREB-2 antibodies (1×5-HT+CREB-2 Ab, both in bold lines) are compared to changes in EPSP amplitude induced by five pulses of 5-HT (5×5-HT) at 2 and 24 hr. While the EPSP facilitation decays rapidly after one pulse of 5-HT (with a return to base line after 10 min), pairing one pulse of 5-HT with injection of anti-ApCREB-2 antibodies induces a long-term facilitation paralleling that of 5×5-HT. This long-term facilitation is abolished by the application of the protein synthesis inhibitor anisomycin (1×5-HT+CREB-2 Ab+ANISO) or the RNA synthesis inhibitor actinomycin D (1×5-HT+CREB-2 Ab+ACTINO) during the training. The difference in EPSP amplitude at 2 hr between 5×5-HT and 1×5-HT+CREB-2 Ab may reflect the transient protein synthesis-dependent, but RNA synthesis-independent component of long-term facilitation 2 hr after 5-HT stimulation (Ghirardi et al., 1995). The controls are either untreated (control), or injected with ApCREB-2 antiserum without 5-HT administration (CREB-2 Ab).

(FIG. 7B) Comparison of the time course of the EPSP amplitude changes in the first 2 hr after application of a single 5 min pulse of 5-HT with or without injection of CREB-2 Ab. The control cells were not exposed to 5-HT.

(FIG. 7C) Example of EPSPs recorded in motoneuron L7 after stimulation of the sensory neuron before (0 hr), 2 hr and 24 hr after 5-HT treatment. One pulse of 5-HT paired with the injection of an ApCREB-2 antiserum induces a significant increase in EPSP amplitude at 2 and 24 hr, but injection the preimmune serum (PRE-CREB-2 Ab) or depleted immune serum does not induce long term facilitation.

(FIG. 7D) Examples of EPSPs recorded at indicated times in cocultures injected with ApCREB-2 antiserum paired with one 5 min pulse of 5-HT.

FIGS. 8A, 8B, 8C and 8D. Summary of the Effects of Injection of ApCREB-2 antiserum on Short- and Long-Term Facilitation.

(FIG. 8A) Injection of ApCREB-2 antiserum paired with one pulse of 5-HT induces a facilitation at 2 hr that is blocked by anisomycin (ANISO) and actinomycin D (ACTINO). The height of each bar corresponds to the mean percentage change ±SEM in EPSP amplitude tested 2 hr after one pulse of 5-HT or of seawater (control cultures, first bar). CREB-2 and C/EBP indicate antisera raised against recombinant ApCREB-2 and ApC/EBP proteins, respectively. CREB-2 depleted indicates the immune anti-ApCREB-2 serum depleted by incubation with bacterial-expressed ApCREB-2 bound to agarose beads. PRE indicates matching preimmune serum. PAS is an antiserum raised against an Aplysia RNA binding Y box protein (Skehel and Bartsch, 1994).

(FIG. 8B) The facilitation induced by one pulse of 5-HT paired with ApCREB-2 antiserum injection lasts 24 hr and is dependent on RNA and protein synthesis. The height of each bar corresponds to the mean percentage change ±SEM in EPSP amplitude tested 24 hr after one 5 min pulse of 5-HT or of seawater (control cultures, first bar).

(FIG. 8C) Long-term facilitation induced by five pulses of 5-HT is not affected by ApCREB-2 antiserum injection. The height of each bar corresponds to the mean percentage change ±SEM in EPSP amplitude tested 24 hr after five 5 min pulses of 5-HT or of seawater (control cultures, first 3 bars). The injection of ApCREB-2 antiserum (third bar) as well as injection of normal rabbit serum (NRS, second bar) without exposure to 5-HT does not induce long-term facilitation.

(FIG. 8D) Short-term facilitation is not affected by injection of ApCREB-2 antiserum. The height of each bar corresponds to the mean percentage change ±SEM in EPSP amplitude tested 1 min after one pulse of 5-HT or of sea water (control cultures, first bar).

Figure 9:
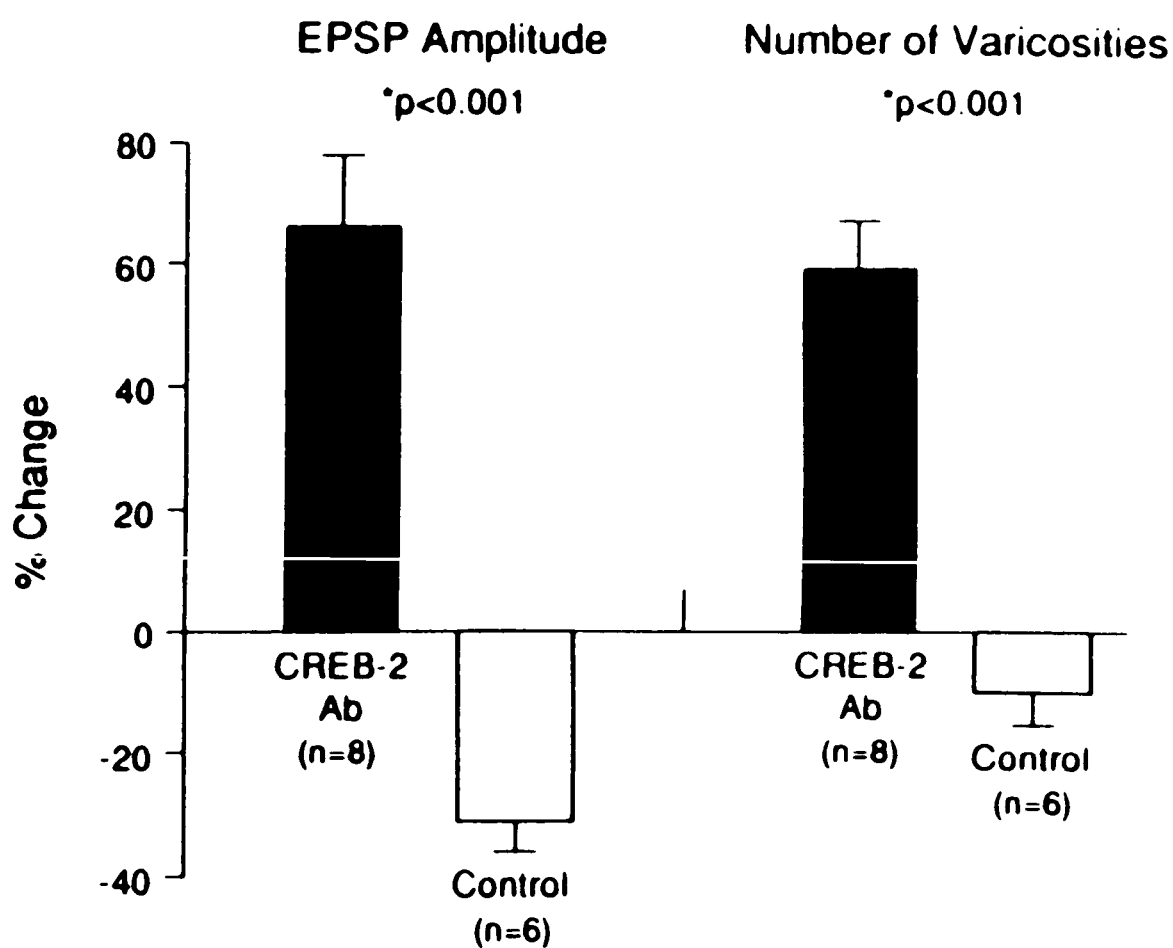

FIG. 9. Summary of Long-Term Functional and Structural Changes Evoked by One Pulse of 5-HT Paired With Injection of ApCREB-2 antiserum.

For the functional changes, the height of each bar is the mean ±SEM of the percent change in the amplitude of the EPSP induced in motor neuron L7 following a single pulse of 5-HT and retested 24 hr later. For the structural changes, the height of each bar represents the mean ±SEM of the percent change in the number of fluorescent varicosities per sensory neuron reexamined 24 hr after one pulse of 5-HT. Injection of the ApCREB-2 antiserum paired with one pulse of 5-HT results 24 hr later in a significant enhancement of the EPSP amplitude and a concomitant significant increase in the number of varicosities.

Figures 10C, 10D:
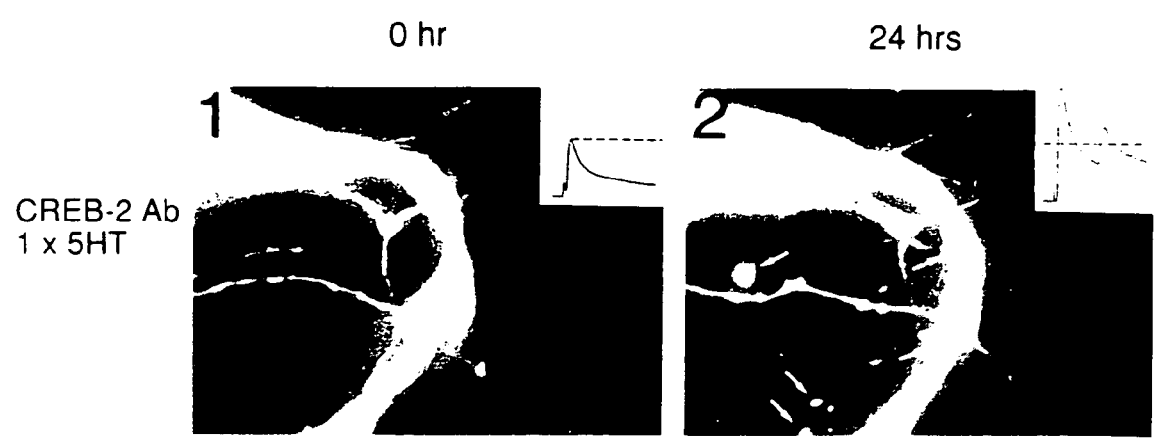

FIG. 10. Examples of Structural Changes Evident 24 hr After One Pulse of 5-HT Paired With Injection of ApCREB-2 Antiserum.

The fluorescent micrographs taken from the same regions of sensory neurites contacting the axon hillock of L7 before (1 and 3) and 24 hr after treatment (2 and 4). Arrows in (2) illustrate examples of some of the new varicosities present one day after one pulse of 5-HT paired with the injection of the ApCREB-2 antiserum. By contrast, cocultures exposed to one pulse of 5-HT in the absence of antiserum injection (4) showed no long-term increases in either the amplitude of the evoked EPSP or in the number of sensory neuron varicosities. All micrographs are composed of superimpositions of labeled sensory neurite images taken from all focal planes of the view area. As a result, the shape of individual varicosities may be obscured. Scale=20 μm. The EPSPs, evoked before (0 hr) and after (24 hr) one pulse of 5-HT in the pictured neurons are indicated in the inserts.

DETAILED DESCRIPTION OF THE INVENTION

The present invention provides for a method to enhance long-term memory in a subject whose cAMP-responsive gene expression is repressed due to binding of a cAMP-response-element-binding-protein-2 to a protein or a DNA associated with cAMP-responsive gene expression, or both, which includes administering to the subject a compound capable of interfering with such binding in an amount effective to interfere with binding of the protein or the DNA so as to thereby derepress cAMP-responsive gene expression in the subject and enhance the subject's long-term memory.

The compound may be an anti-cAMP-response-element-binding-protein-2 antibody. The compound may be capable of altering phosphorylation of the cAMP-response-element-binding-protein-2. The compound may be an organic compound, a peptide, a peptide mimetic, a small molecule, or a nucleic acid. The protein associated with cAMP-responsive gene expression may include a cAMP-response-element-binding-protein-1, a C/EBP protein, an *Aplysia* ApC/EBP protein, a human C/EBPβ protein, an AF-1 protein, a c-jun protein, a fla protein, or a c-Fos protein. The administration may include intralesional, intramuscular or intravenous injection; infusion; liposome mediated delivery; viral infection; gene bombardment; topical, nasal, oral, anal, ocular, cerebro-spinal, or otic delivery.

Another embodiment of the subject invention may be a method for evaluating the ability of a compound to interfere with binding of a cAMP-response-element-binding-protein-2 to a protein associated with cAMP-responsive gene expression in a cell which includes:

(a) contacting the cell with the compound under suitable cell culture conditions;

(b) measuring the amount of unbound protein associated with cAMP-responsive gene expression in the cell;

(c) comparing the amount in step (b) with the amount of unbound protein associated with cAMP-responsive gene expression in the absence of the compound, so as to thereby evaluate the ability of the compound to interfere with binding of the cAMP-response-element-binding-protein-2 to the protein.

Another embodiment of the present invention is a method for evaluating the ability of a compound to interfere with binding of a cAMP-response-element-binding-protein-2 to a DNA associated with cAMP-responsive gene expression in a cell which includes:

(a) contacting the cell with the compound under suitable cell culture conditions;

(b) measuring the amount of unbound DNA associated with cAMP-responsive gene expression in the cell;

(c) comparing the amount in step (b) with the amount of unbound DNA associated with cAMP-responsive gene expression in the absence of the compound, so as to thereby evaluate the ability of the compound to interfere with binding of the cAMP-response-element-binding-protein-2 to the DNA.

Another embodiment of the present invention is a method for treating a subject with a long-term memory defect due to binding of a cAMP-response-element-binding-protein-2 to a protein or a DNA associated with cAMP-responsive gene expression, or both, which includes administering to the subject a compound capable of interfering with such binding in an amount effective to interfere with the binding of the protein or the DNA so as to thereby treat the subject's long-term memory defect.

The long-term memory defect may include age-related memory loss, Alzheimer's Disease, amnesia, ischemia, shock, head trauma, neuronal injury, neuronal toxicity, neuronal degradation, Parkinson's disease, or senility. The compound may comprises an anti-cAMP-response-element-binding-protein-2 antibody. The protein may include a cAMP-response-element-binding-protein-1, a C/EBP protein, an *Aplysia* ApC/EBP protein, a human C/EBPβ protein, an AF-1 protein, a c-jun protein, a fla protein, or a c-Fos protein. The cAMP-response-element-binding-protein-2 may include human CREB2 transcription factor, murine ATF4 transcription factor, or *Aplysia* ApCREB2 transcription factor. The administration may include intralesional, intramuscular or intravenous injection; infusion; liposome mediated delivery; viral infection; gene bombardment; topical, nasal, oral, anal, ocular, cerebro-spinal, or otic delivery.

The present invention provides for a recombinant eukaryotic cell including a DNA encoding a cAMP-response-element-binding-protein-2 not naturally present in the cell, operatively linked to a promoter capable of directed enhanced expression of the DNA, the DNA and the promoter being stably integrated into the genome of the eukaryotic cell.

The present invention provides for a transgenic, non-human mammal whose somatic and germ cells contain and express a DNA encoding a cAMP-response-element-binding-protein-2 not naturally occurring in the non-human mammal, operatively linked to a promoter capable of directed enhanced expression of the DNA, the DNA and the promoter being stably integrated into the genome of the non-human mammal.

The present invention further provides for a pharmaceutical composition which includes an effective amount of a compound capable of interfering with binding of a cAMP-response-element-binding-protein-2 to a protein associated with cAMP-responsive gene expression in a cell and a pharmaceutically acceptable carrier. The carrier may be a diluent, an aerosol, a topical carrier, an aqueous solution, a nonaqueous solution, or a solid carrier. The carrier may include an appropriate adjuvant, a herpes virus, a liposome, a microencapsule, a neuronal cell receptor ligand, a neuronal-specific virus, a polymer encapsulated cell, or a retroviral vector.

As used herein "cAMP-response-element-binding-protein-2" encompasses CREB2, *Aplysia* CREB2 transcription factor protein, *Aplysia* CREB2 transcription factor nucleic acid, ApCREB2, human CREB2 transcription factor protein, human CREB2 transcription factor nucleic acid, murine ATF2 transcription factor protein, murine ATF2 transcription factor nucleic acid and natural variants thereof. Such variants encompass homologues of CREB2 in human, mouse, *Drosophila*, pig, dog, horse, monkey, *C. Elegans* and *Aplysia*.

As used herein "subject" encompasses a mammal, a human, a primate, a dog, a swine, an *aplysia* or a mouse.

Trangenics

This invention provides a transgenic nonhuman mammal whose somatic and germ cells contain and express a gene coding for a cAMP-response-element-binding-protein-2 not naturally occurring in the non-human mammal. The gene, having been introduced into the nonhuman mammal, or an ancestor of the nonhuman mammal at the single cell stage or an embryonic stage, is operably linked to a promoter and integrated into the genome of the nonhuman mammal. One skilled in the art would be familiar with the experimental methods necessary to produce a transgenic mammal, e.g. Leder et al., U.S. Pat. No. 4,736,866 and Krimpenfort and Berns, U.S. Pat. No. 5,175,384 and Wagner and Chen, U.S. Pat. No. 5,175,385. Preferably, the nonhuman mammal may be a mouse. The gene may be a combination of human cAMP-response-element-binding-protein-2 nucleic acid sequences and adjacent, homologous nonhuman mammal apolipoprotein-J nucleic acid sequences. The promoter may be a nerve tissue specific promoter such as the mouse neurofilament-light gene promoter or the rat neuronal specific enolase promoter (Forss-Petter et al., 1990), which is effective for the expression of the gene in neuronal cells of the brain. The human platelet-derived growth factor-β gene promoter, which is effective for the expression of the gene in cells of the brain may also be utilized. Other nerve tissue specific promoters which may be used are rat sodium channel gene promoter (Maue et al., 1990), the human APP gene promoter (Wirak et al., 1991) and mouse mylein basic protein gene promoter (Readhead et al., 1987). A yeast artificial chromosome construct containing the human cAMP-response-element-binding-protein-2 gene may also be utilized.

This invention provides a nonhuman mammal whose neuronal cells or glial cells or both, express a cAMP-response-element-binding-protein-2 gene. Preferably, the nonhuman mammal may be a mouse. The gene, having been introduced into the mouse by localized infection with retrovirus, is operably linked to a promoter. The retrovirus has an inducible retroviral vector consisting of a marker gene, a constitutive promoter and an inducible promoter. Retroviral-mediated gene transfer is a procedure known to individuals skilled in the art. Procedures for the infection of neuronal progenitor cells have been established, see, for example, Levison and Goldman (1993).

CREB2-containing retroviral expression constructs may be introduced into fetal and neonatal animals by direct viral infection of subventricular zone (primitive neuronal and glial precursor) cells (see Levison and Goldman, 1993). In this protocol, the CREB2 constructs may be cloned downstream of a constitutive promoter (e.g. SV40) in tandem with a beta-galactosidase gene under the control of the retroviral long terminal repeat (LTR) promoter. Thus, CREB-2-producing retrovirally infected cells will be specifically marked by β-galactosidase enzymatic activity (i.e. blue stain in tissue sections). It would then be possible to search for effects of local CREB2 protein overexpression in the intact animal brain on neuronal morphology, amyloid deposition, tau protein phosphorylation and determine whether these effects differ for each CREB2 isoform. If pathological changes are observed, then these animals would serve as a useful in vivo assay system for pharmacological agents.

The transgenic nonhuman mammals may provide an experimental medium for elucidating aspects of long-term facilitation and memory and to serve as tools for screening drugs that may have potential application as therapeutic agents to prevent or limit memory defects. Transgenic nonhuman mammals provide both a prognostic and diagnostic means for the study of memory, in particular for determining the efficacy of pharmaceutical drugs in treating a subject.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Transcription Factor CREB2/ATF4 as a Repressor of Memory and a Potential Target of Drugs for Improvement of Memory Formulation A transcription factor CREB2 has been identified as a repressor of long-term facilitation in *Aplysia* neurons. Injection of anti-CREB2 antibodies into sensory neurons has been shown to interfere with CREB2 function and causes a single pulse of serotonin (5-HT). This pulse of serotonin ususally induces only short term facilitation lasting minutes, however, under these conditions (with anti-CREB2), serotonin evokes facilitation lasting more than one day. This facilitation has the properties characteristic of long-term facilitation. Specifically, it requires transcription and translation, it induces growth of new synaptic connections and finally it occludes further facilitation by five pulses of 5-HT.

It has been demonstrated that similar to its human homologue CREB2, *Aplysia* CREB2 is a repressor of the transcriptional activator CREB1. Furthermore, both *Aplysia* CREB2 and its mammalian homologue ATF4 both heterodimerize, and are repressors of the transcriptional activators ApC/EBP and C/EBPβ, respectively. Another transcriptional activator has also been identified, AF-1, which is necessary for the establishment of long-term facilitation. AF-1 has been demonstrated to interact with CREB2.

Therefore, CREB2 blocks the transition from short term to long-term facilitation by interacting with transcriptional activators necessary for development of long-term facilitation. Long-term facilitation is a close cellular correlate to long-term memory in *Aplysia*. It is possible, therefore, that CREB2 blocks the transition from short-term memory to long-term memory in both *Aplysia* and mammals, including humans. Certain defects in memory formation, in particular the age-related memory loss, may represent in part the inability to remove such repression. Repression of memory mediated by CREB2 and the CREB2 protein itself can be targets for developing drugs for use in the treatment of memory defects. The use may extend to memory defects which are related to Alzheimers disease and other diseases or trauma.

Example 2

CREB-2/ATF-4 as a Repressor of Long-Term Facilitation in *Aplysia*: Relief of Repression Converts a Transient Facilitation into a Long-Term Functional and Structural Change Summary The switch from short- to long-term facilitation induced by behavioral sensitization in *Aplysia* involves CREB-like proteins, as well as the immediate-early gene ApC/EBP. Using the bZIP domain of ApC/EBP in a two-hybrid system, we have cloned ApCREB-2, transcription factor constitutively expressed in sensory neurons which resembles human CREB-2 and mouse ATF-4. ApCREB-2 represses ApCREB-1 mediated transcription in F9 cells. Injection of anti-ApCREB-2 antibodies into *Aplysia* sensory neurons causes a single pulse of serotonin (5-HT), which induces only short-term facilitation lasting minutes, to evoke facilitation lasting more than one day. This facilitation has the properties of long-term facilitation: it requires transcription and translation, induces the growth of new synaptic connections, and occludes further facilitation by five pulses of 5-HT. In cell culture, as in the intact ganglion, both short- and long-term facilitation involve an enhancement of transmitter release induced by cAMP and mediated by the cAMP dependent protein kinase (PKA) (Brunelli et al., 1976, Schacher et al., 1988; Scholz and Byrne, 1988; Ghirardi et al., 1992). With repeated pulses of 5-HT, which give rise to long-term facilitation, the intracellular cAMP concentration increases (Bernier et al., 1982) and the catalytic subunit of PKA translocates to the nucleus of the sensory neurons (Bacskai et al., 1993), where it appears to phosphorylate one or more cAMP response element-binding proteins (CREB-like transcription factors), thereby activating cAMP-inducible gene expression (Kaang et al., 1993). Injection of an oligonucleotide containing the somatostatin cAMP response element (CRE) into the nucleus of a sensory neuron selectively blocks the long-term enhancement in synaptic strength induced by 5-HT without affecting the short-term process (Dash et al., 1990). An *Aplysia* homolog of CREB-1 has recently been cloned. ApCREB-1 has 42% homology with the mouse CREB-1 over the whole length of the protein, while the basic region/leucine zipper (bZIP) and the phosphorylation domain (P-box), characteristic of CREB-1, are 96% and 90% identical, respectively. Similar to its mammalian homologues, ApCREB-1 binds to the CRE in vitro and is a PKA dependent transactivator (Bartsch et al., in preparation).

In sensory neurons, 5-HT and cAMP induce the immediate-early gene ApC/EBP, a transcription factor necessary for the establishment and maintenance of the stable, self-maintained structural changes characteristic of the long-term memory process (Bailey and Chen, 1983; 1988; 1989; Glanzman et al., 1990). There is apparent generality of CREB-1 as a component of the switch between short-term and long-term memory in *Aplysia, Drosophila*, mice and perhaps humans. (Yin et al., 1994,1995; Bourtchuladze et al., 1994., Petrij et al., 1995) It is a question as to whether ApCREB-1 and ApC/EBP can recruit additional transcription factors in the sensory neurons following sensitizing stimuli.

Results

Cloning of ApCREB-2 by its Interaction with ApC/EBP in the Yeast Two-Hybrid System.

The C-terminal portion of ApC/EBP containing the basic region/leucine zipper (bZIP) domain was used to screen an *Aplysia* CNS specific cDNA library by the yeast two-hybrid system (Fields and Song, 1989; Chien et al., 1991). Two independent clones contained an identical open reading frame of 1134 bp encoding a putative 378 amino acids polypeptide (FIG. 1A). The 118 C-terminal amino acids (amino acids 260-378) of the predicted polypeptide contain a bZIP motif (Landschulz et al., 1988, Vinson et al., 1989) that interacts with ApC/EBP (FIG. 6C). In addition to interacting with ApC/EBP, both the full-length 378 amino acid protein and the C-terminal 118 amino acid peptide interact with mammalian CREB-1 and c-fos proteins in the two-hybrid system.

The predicted polypeptide shows highest sequence homology to the amino acid sequences of two transcription factors: human CREB-2 (hCREB-2) [(Karpinski et al., 1992); also ATF-4 or TAXREB 67 (Hai et al., 1989, Tsujimoto et al., 1991)] and mouse ATF-4 (mATF-4) [(Mielnicki and Pruitt, 1991), also C/ATF (Vallejo et al., 1993)]. Therefore the *Aplysia* polypeptide has been termed ApCREB-2. Over the whole length of the protein ApCREB-2 shares 21% identical amino acids with hCREB-2 and mATF-4. In the bZIP domain, ApCREB-2, mATF-4, and hCREB-2 are 50% identical (FIG. 1B). Unlike hCREB-2 or mATF-4, ApCREB-2 contains a second heptad repeat of hydrophobic amino acids near the N-terminus (aa 73–108), which could potentially form a second leucine zipper (FIG. 1A). However, this domain does not mediate ApCREB-2 homodimerization or the interaction with the bZIP domain of ApC/EBP (FIG. 6C).

ApCREB-2 is Expressed in the Nervous System of *Aplysia*.

ApCREB-2 is expressed at high levels in the CNS and the gill, but is detectable at low levels by Northern blot in all *Aplysia* tissues tested (FIG. 2A). This relatively restricted expression of ApCREB-2 mRNA contrasts with the more ubiquitous expression of its closest homologs, mATF-4 and hCREB-2 (Tsujimoto et al., 1991; Chevray and Nathans, 1992; Vallejo et al., 1993; Jungling et al., 1994).

In Western blots of *Aplysia* CNS extracts, polyclonal ApCREB-2 antiserum raised against full length recombinant ApCREB-2 and the affinity-purified anti-ApCREB-2 antibody recognize a protein that migrates as multiple bands with an apparent molecular weight of around 50 kD (FIGS.

2B and 2C). This molecular weight is higher than that 42 kD deduced from the ApCREB-2 cDNA, but it is consistent with the apparent molecular weight of in vitro translated ApCREB-2 and ApCREB-2 immunoprecipitated from extracts of the *Aplysia* nervous system (FIG. 2C). Although both the preimmune antisera and the anti-ApCREB-2 antisera recognize additional proteins in Western blots of *Aplysia* CNS extracts, the major 50 kD signals are not detected by the preimmune serum (FIG. 2B, lane 2), or by the ApCREB-2 antiserum preincubated with recombinant ApCREB-2. (FIG. 2B, lane 3). The strong signal at 40 kD and several weaker signals are recognized by both immune, blocked immune and preimmune antisera. Therefore, preimmune sera has been used and blocked immune antisera has been used as matching controls in electrophysiological experiments described below.

ApCREB-2 is Constitutively Expressed in Sensory Neurons.

To determine whether ApCREB-2 is expressed in the neurons that exhibit long-term presynaptic facilitation, RT-PCR was used to examine the expression of ApCREB-2 mRNA in cultures of *Aplysia* sensory neurons. We detected ApCREB-2 mRNA both in nontreated cultures of sensory neurons and in cultures exposed to repeated pulses of 5-HT. (FIG. 3A). ApCREB-1 mRNA was also detected in untreated *Aplysia* sensory neurons by RT-PCR (Bartsch et al., in preparation). In addition, the steady state levels of ApCREB-2 and ApCREB-1 mRNAs were not affected either in vivo or in vitro by exposure to 5-HT which induces the mRNA level of ApC/EBP (FIG. 3B). Furthermore the level of ApCREB-2 mRNA does not change following exposure to agents that increase cAMP (forskolin, IBMX, 8-bromo cAMP and Sp-cAMPS), application of the PKA inhibitor Rp-cAMPS, calcium iontophore A23187, phorbol esters, okadaic acid, the protein synthesis inhibitor anisomycin or neuronal injury. These results indicate that ApCREB-2 and ApCREB-1 are coexpressed in sensory neurons and the steady state level of ApCREB-2 mRNA is not regulated by 5-HT, cAMP or cytoplasmic $Ca^{2+}$ levels.

ApCREB-2 is a Substrate for Protein Kinases.

The primary structure of ApCREB-2 has putative phosphorylation sites for both PKC and MAP kinases (FIG. 1A). Furthermore, ApCREB-2 is a substrate for PKC, MAP kinase, PKA, and CaM kinases in vitro. The phosphorylation of ApCREB-2 in vitro results in an increase of apparent molecular weight of the phosphoprotein in SDS gels. A similar shift in molecular weight is detected by Western blots of *Aplysia* CNS extracts isolated from animals exposed to 5-HT in vivo. Exposure to 5-HT does not affect the protein level of ApCREB-2 or ApCREB-1 in the *Aplysia* CNS. By contrast, ApC/EBP protein in the same CNS extracts becomes detectable only after 60 min of 5-HT exposure in vivo (FIG. 4A). The shift in apparent molecular weight of ApCREB-2 following 5-HT treatment in vivo presumably is the result of phosphorylation, since phosphatase treatment of the CNS extract results in the increased migration of ApCREB-2 in SDS-PAGE (FIG. 4B).

ApCREB-2 is a Repressor of ApCREB-1 Mediated Activation in F9 Cells.

Human CREB-2 represses CREB-1 mediated transcriptional activation in CV-1 cells and neurons (Karpinski et al., 1992; Jungling et al., 1994). Whether ApCREB-2 could also function as a repressor of ApCREB-1 mediated transactivation in transfected undifferentiated mouse F9 cells was examined. The ability of ApCREB-2 and ApCREB-1 to regulate a minimal control region (a single CRE in front of a minimal SV40 promoter) of a pGL3-CRE luciferase reporter gene was first examined. ApCREB-1 activates this minimal CRE reporter in a PKA dependent manner (relative activation 2.13±0.26 without and 10.50±1.42 with the PKA) and is repressed by ApCREB-2 upon cotransfection in the absence and presence of PKA catalytic subunit (relative activation 0.96±0.15 and 1.64±0.20, respectively) (FIG. 5A). The degree of ApCREB-1 repression by ApCREB-2 is dependent on the concentration of ApCREB-2. ApCREB-2 does not activate this minimal CRE reporter.

In previous experiments, Kaang et al. (1993) demonstrated that a 5xCRE-VIP-lacZ reporter is activated by 5-HT and cAMP in *Aplysia* sensory neurons. We therefore also cotransfected ApCREB-2 and ApCREB-1 were cotransfected with this reporter. Upon cotransfection, ApCREB-2 again abolished the transcriptional activity of ApCREB-1 both in the absence and in the presence of PKA (relative activation 1.84±0.25 and 4.12±0.53, respectively, as compared to 2.13±0.30 and 48.60±5.23 for ApCREB-1 alone.) (FIG. 5B). Similarly, ApCREB-2 repressed transactivation mediated by rat CREB-1 (relative activation 2.27±0.3 and 5.15±0.62 as compared to 7.65±0.65 and 68.82±7.3 for rat CREB-1 alone, without and with PKA, respectively).

Thus this data suggest that ApCREB-2 can repress both ApCREB-1 and rat CREB-1 mediated transactivation from a CRE and are consistent with the possibility that ApCREB-2 and ApCREB-1 may interact directly on the CRE.

ApCREB-2 can be an Activator in the Absence of ApCREB-1.

In addition to repressing transcription mediated by ApCREB-1, it was found that ApCREB-2 can also function as an activator of the 5xCRE-VIP-lacZ reporter gene in F9 cells. ApCREB-2 transactivation in F9 cells is stimulated by PKA to the level comparable with ApCREB-1 (relative activation 2.46±0.2 without and 43.12±5.1 with PKA)(FIG. 5B). Both the full length ApCREB-2 protein and its N terminal 288 amino acids are strong activators of the reporter UASg-lacZ gene when fused to the GAL4 DNA binding domain (relative activity 82%±27 and 59%±18, respectively, as compared to wild type GAL4). Thus, ApCREB-2 has an internal transcription activation domain in its N-terminal 280 amino acids and can under certain circumstances be a transcriptional activator. Unlike ApCREB-1, ApCREB-2 cannot activate a minimal, single copy CRE driven construct (FIG. 5A). Thus, the activating and repressing potential of ApCREB-2 and ApCREB-1 on the CRE are not fully symmetrical. The ability of ApCREB-2 to activate from the CRE is more restricted than its ability to repress ApCREB-1 injury.

ApCREB-2 is a CRE Binding Protein.

The DNA binding specificity of ApCREB-2 was examined in a binding site selection assay using bacterial-expressed recombinant ApCREB-2 protein to select optimal binding sequences from a pool of randomly generated DNA targets. This assay identified a binding sequence (BS1) for ApCREB-2 which resembles the CRE DNA-binding sequence of the CREB/CREM/ATF family of transcription factors, as well as the CAAT DNA binding motif of the C/EBP family of transcription factors (FIG. 6A). The DNA binding capability of ApCREB-2 by electrophoretic mobility shifts using both symmetrical and asymmetrical CREs and CAAT motifs of C/EBP binding sites was then reexamined. Purified bacterial-expressed ApCREB-2 protein binds in solution the symmetrical CRE of the somatostatin gene, the core CRE palindrome, the asymmetrical CRE of the enkephalin gene and the BS1 DNA binding site. However, ApCREB-2 did not bind to the asymmetrical CRE of the phosphoenolpyruvate carboxykinase gene or to the asymmetrical putative CRE site of the ApC/EBP gene. In addition, ApCREB-2 did not bind to any of the CAAT DNA-binding sites tested (FIG. 6B). The binding affinity of ApCREB-2 to CRE was low, perhaps because of inefficient homodimer formation. Deleting the 260 N-terminal amino acids of ApCREB-2, which removes the second leucine zipper motif, greatly increases the efficiency of homodimer formation. This deletion does not affect heterodimer formation as both the full-length and the N-terminal deletion mutant of ApCREB-2 heterodimerize with the same high affinity with ApC/EBP (FIG. 6C). Thus, ApCREB-2 forms weak homodimers on CRE, perhaps due to the presence of an inhibitory structure in the N-terminal part of the protein. In contrast to its ability to form only weak homodimerizers we have found that ApCREB-2 can effectively heterodimerize with other b-ZIP transcription factors. In some experiments, it was found that in addition to ApC/EBP, ApCREB-2 forms in vitro heterodimers with ApCREB-1, with rat CREB-1 and with c-fos proteins.

One Pulse of 5-HT Produces Long-Term Facilitation when Paired with Injection of ApCREB-2 Antiserum.

Figure 7A:
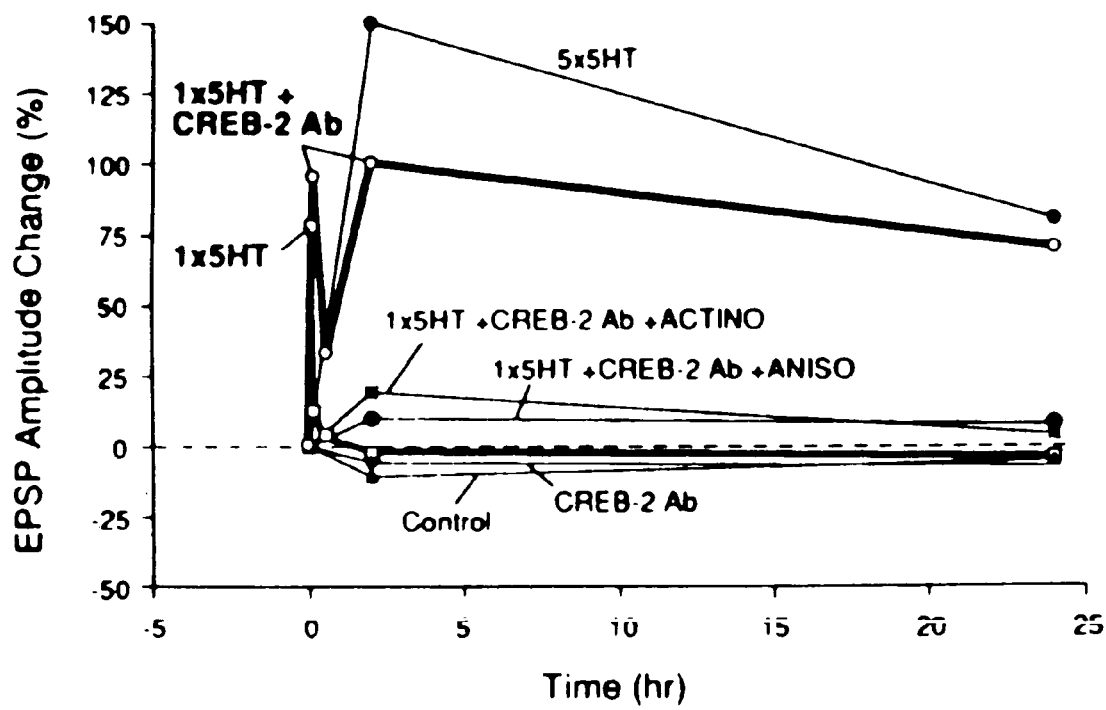
Figure 7B:
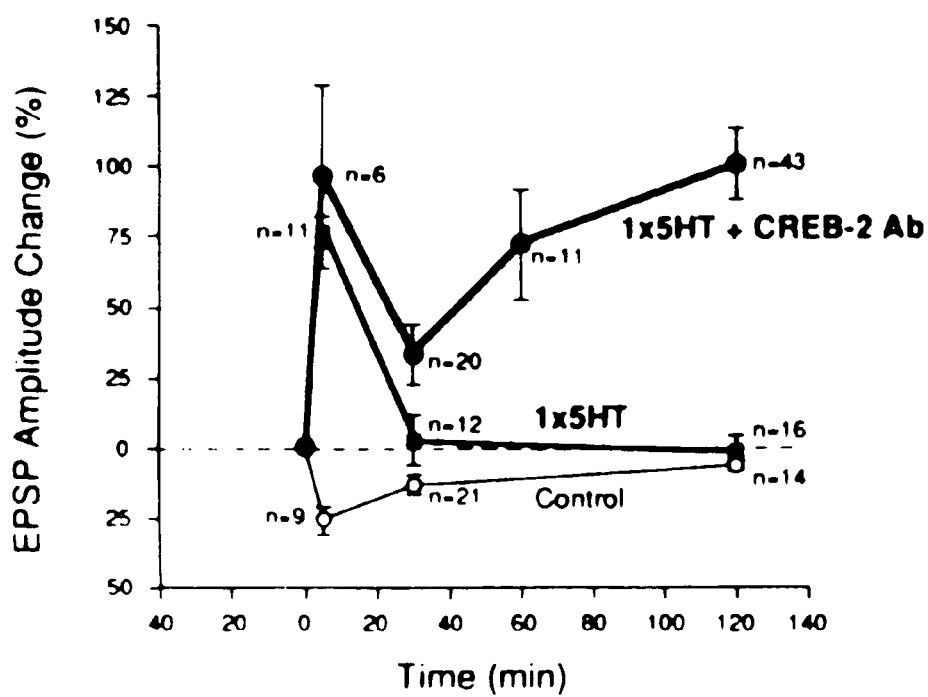
Figure 7C:
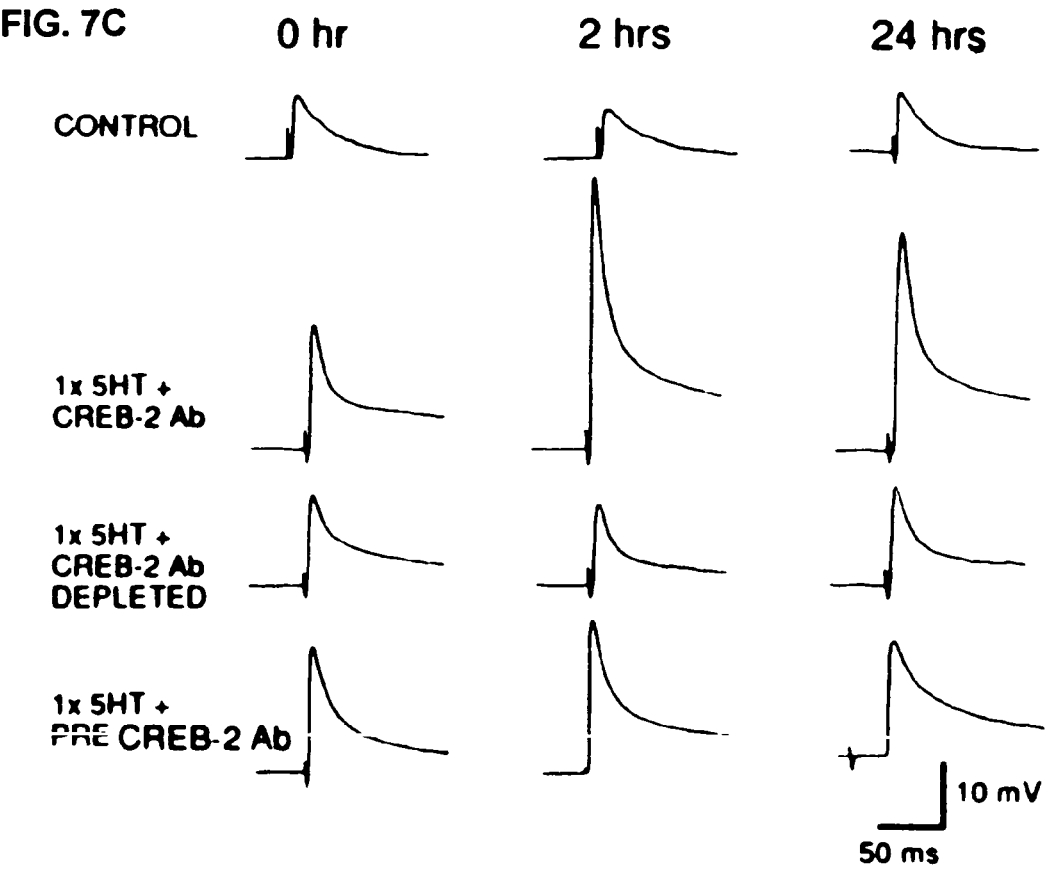
Figure 7D:
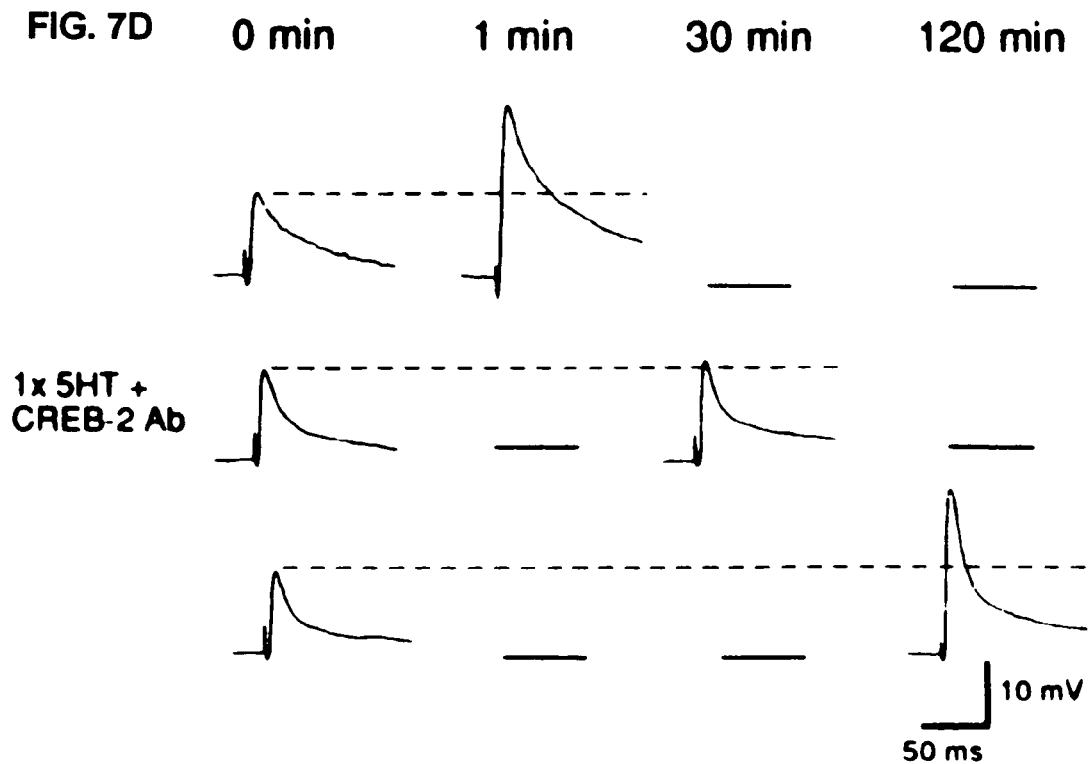

In both the intact *Aplysia* and in neuronal cell culture, five pulses of 5-HT induce long-term facilitation in the connections between the sensory and motor neurons lasting 24 hr or more. By contrast, a single pulse of 5-HT produces only a short-term facilitation lasting about 10 min (FIGS. 7A and B). This single pulse increases the excitatory postsynaptic potential (EPSP) evoked in the motor cell by stimulating a single sensory neuron by 76.7% at 1 min after 5-HT exposure (±5.4, n=11 p<0.01 compared to control cells). This facilitation decays to 13.6% at 10 min (±18.7, n=5), and to 2.83% at 30 min (±8.8, n=12). Two hours after a single pulse of 5-HT the change in EPSP amplitude has returned to control level (−1%±5.7, n=16) and it remains there at 24 hr (−4.12%±6.09, n=8).

To determine whether ApCREB-2 could also act as a functional repressor and parallel its action as a transcriptional repressor of ApCREB-1 in transfection assays, we injected ApCREB-2 antiserum into the sensory neurons 1 hr before exposure to single or multiple pulses of 5-HT. In the presence of the antiserum, rather than producing the short-term facilitation lasting 10 min, one pulse of serotonin produced facilitation lasting more than 24 hour. This facilitation was robust; it was seen in 42 out of 43 cells. Moreover, the facilitation seen at 24 hr was comparable in magnitude to that seen at 24 hr with five pulses of 5-HT.

Figure 8A:
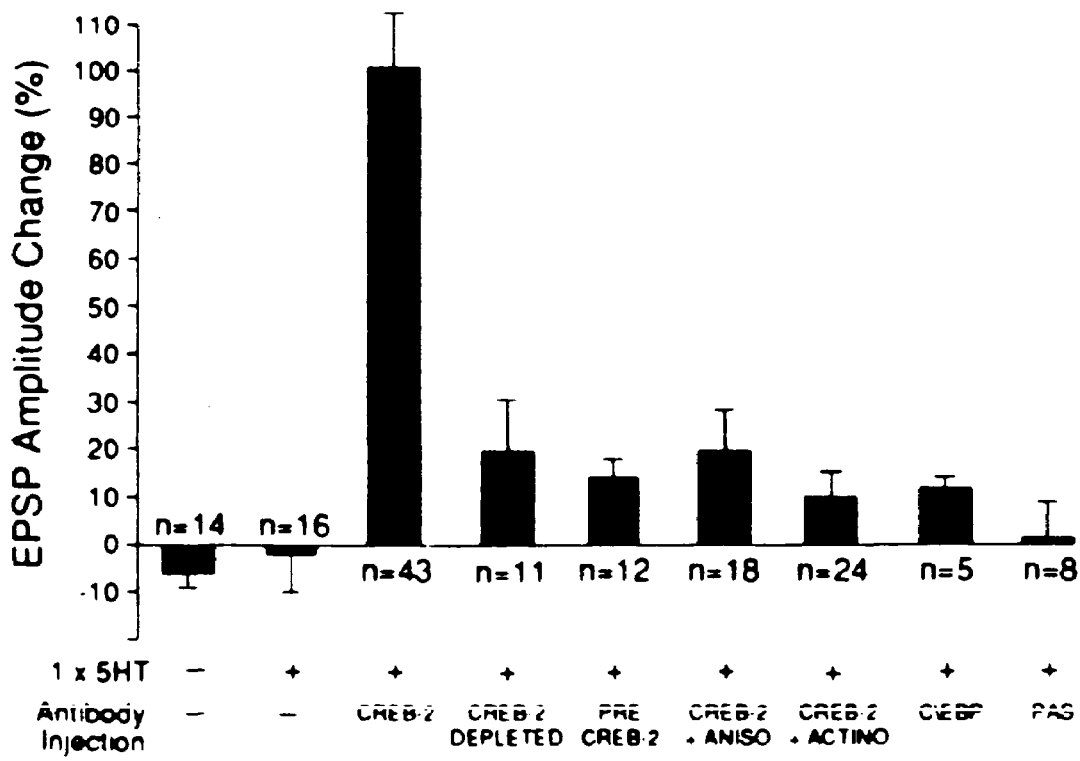

The long-term facilitation following five pulses of 5-HT is seen as early as 2 hr after the first pulse (FIG. 7A and Ghirardi et al., 1995). This early component of long-term facilitation has a larger amplitude than the facilitation evident at 24 hr, but it differs mechanistically from the facilitation evident at 24 hr in that it is only partially (about 70%) dependent on RNA synthesis, although it is completely dependent on protein synthesis. When a single pulse of 5-HT is paired with the injection of ApCREB-2 antiserum, there is also a significant facilitation present at 2 hr [+100.95% (±12.52, n=43 p<0.01)] and this facilitation persisted 24 hr later, when the synaptic potential is still significantly facilitated [+70.05%(+7.65, n=42, p<0.01) (FIGS. 7A, 8A and B)]. By contrast cultures treated with one pulse of 5-HT and injected with serum depleted of anti-ApCREB-2 antibody or with preimmune serum shows no significant facilitation, either at 2 hr (+19.64%±10.56, n=11 and +13.75%±4.05, n=12, respectively), or at 24 hr (−4.27%±9.70, n=11 and +1.5%±11.57, n=12, respectively) compared to the noninjected control cells not exposed to 5-HT (−6.21%±2.10, n=14 at 2 hr, and −0.33%±4.56, n=9 at 24 hr) (FIGS. 8A and B). As an additional control, a single pulse of 5-HT was paired with the injection of two unrelated antibodies (anti-ApC/EBP Ab, anti-PAS Ab). In both cases no significant facilitation was found either at 2 hr (+11.8%±5.51, n=5 and +1.87%±6.29, n=8, respectively) or at 24 hr (+1.8%±9.77, n=5, and +3.62%±11.97, n=8, respectively) (FIGS. 8A and B). These results were obtained using a single ApCREB-2 antiserum. However, injection of a second independently raised ApCREB-2 antiserum yielded comparable results.

Facilitation Produced by One Pulse of 5-HT Paired with Injection of ApCREB-2 Antiserum has the Properties of Transcriptionally-Dependent Long-Term Facilitation.

Figure 8B:
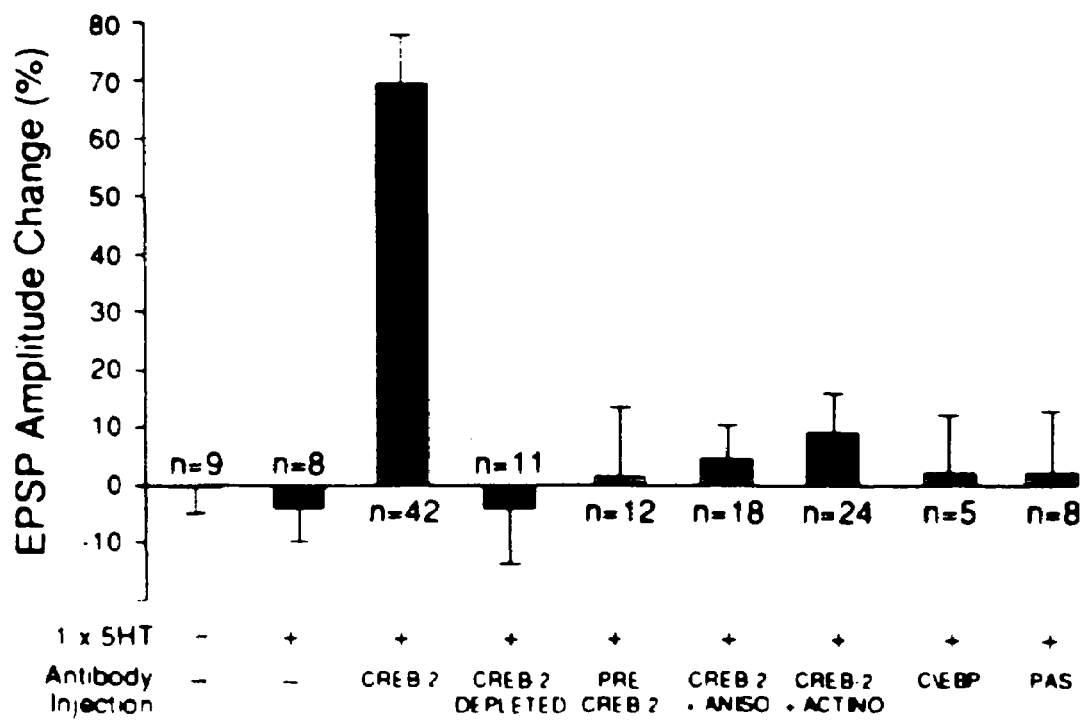

Long-term facilitation induced by repeated pulses of 5-HT requires protein and RNA synthesis. (Montarolo et al., 1986; Bailey et al., 1992). The effect of the protein synthesis inhibitor anisomycin and the RNA synthesis inhibitor actinomycin D was examined on the synaptic modifications produced at 2 and 24 hr after the injection of ApCREB-2 antiserum paired with the application of a single pulse of 5-HT. Incubating sensory-motor neuron cocultures with anisomycin during a single pulse of 5-HT blocks the increase in amplitude of synaptic potential after injection with ApCREB-2 antiserum, both at 2 hr after exposure (+19.17%±6.85, n=18) and at 24 hr (+3.67%±5.54, n=18) (FIGS. 7A, 8A and 8B). Similar results were obtained using actinomycin D, where the facilitation at 2 hr was reduced to +10.12% (±5.10, n=24), and at 24 hr to 7.87% (±5.84, n=24, FIGS. 7A, 8A and 8B).

Figure 8C:
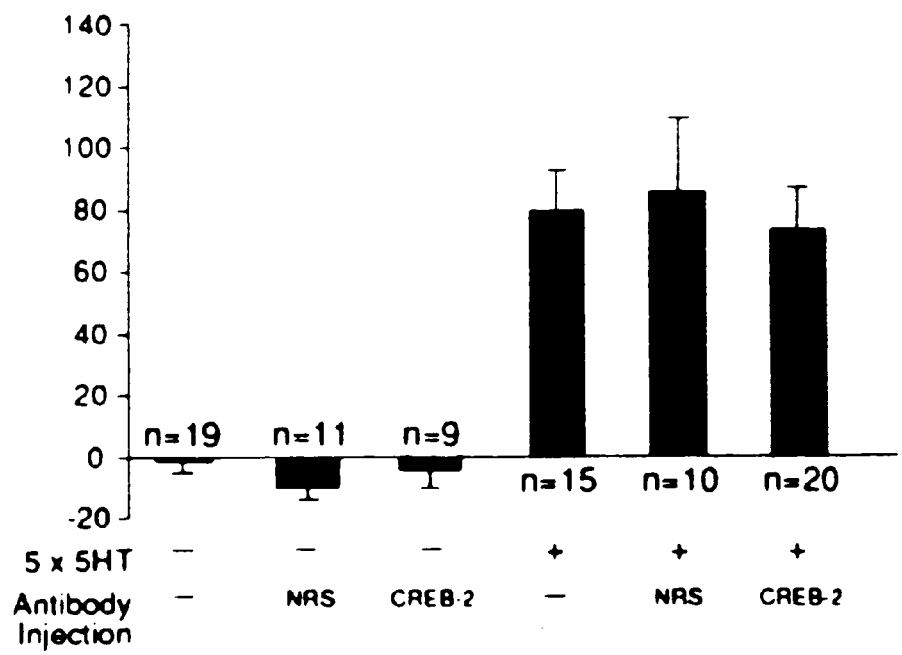

If one pulse of 5-HT in the presence of ApCREB-2 antiserum phenocopies long-term facilitation, the injection of antibody should also occlude the effects of five pulses of 5-HT. In the cocultures injected with ApCREB-2 antiserum, the facilitation measured 24 hr after five pulses of 5-HT was not significantly greater (+74.5%±13.56, n=20) than the facilitation obtained in cells exposed to five pulses of 5-H and not injected with antibody (+79.6%±12.95, n=15), or cells treated with five pulses of 5-HT and injected with normal rabbit serum (+91.6%±21.31, n=10) (FIG. 8C). Injection of ApCREB-2 antiserum alone, without 5-HT treatment, induced a slight decrease in the strength of the connection (−5.11%±5.03, n=9), similar to that found in the control cocultures. In conclusion, the facilitation produced by one pulse of serotonin in the presence of the antibody has properties similar to that induced by five pulses of 5-HT and occludes the effect of five pulses.

The facilitation produced at 2 hr by five pulses of 5-HT is completely blocked by inhibitors of protein synthesis, but is only partially blocked by inhibitors of transcription (Ghirardi et al., 1995). This suggests that five pulses of 5-HT modulate both transcription and translation. Since ApCREB-2 presumably acts only on the transcriptional component of long-term facilitation, one might predict that the pairing of one pulse of 5-HT with injection of ApCREB-2 antiserum with would produce less facilitation at 2 hr than 5 pulses of 5-HT. The facilitation at 2 hr produced by one pulse of 5-HT in the presence of ApCREB-2 antibody is approximately 30% less than that produced by five pulses of 5-HT (FIG. 7A). Similarly, injection of CRE oligonucleotides, which would also likely to affect only the transcriptional component of 2 hr facilitation produced a comparable inhibition at 2 hrs [EPSP increase to +68.29% (18.76, n=14)], thus supporting the suggestion that the role of ApCREB-2 is specific to the transcriptional response to 5-HT.

Facilitation Induced by one Pulse of 5-HT Paired with Injection of ApCREB-2 Antiserum has Two Distinct Phases The facilitation induced by one pulse of 5-HT paired with injection of ApCREB-2 antiserum shows two temporal stages: the first phase is similar both in amplitude and time course to the short-term facilitation induced by one pulse of 5-HT in the absence of the antibody (FIGS. 7A and B). Thus, in the presence of ApCREB-2 antiserum the facilitation also peaks at 1 min and decays at 30 min to 33.3% (±10.44, n=20), but instead of decaying progressively and completely back to baseline at 30 min as in uninjected cells, a second phase of facilitation emerges. At 1 hr this facilitation reaches +72% (±19.74, n=11) and at 2 hr it is about +100.95% (±12.52, n=43). This second phase presumably represents the gradual induction of the transcriptional components of long-term facilitation.

Injection of ApCREB-2 Antiserum does not Affect Short-Term Facilitation.

Figure 8D:
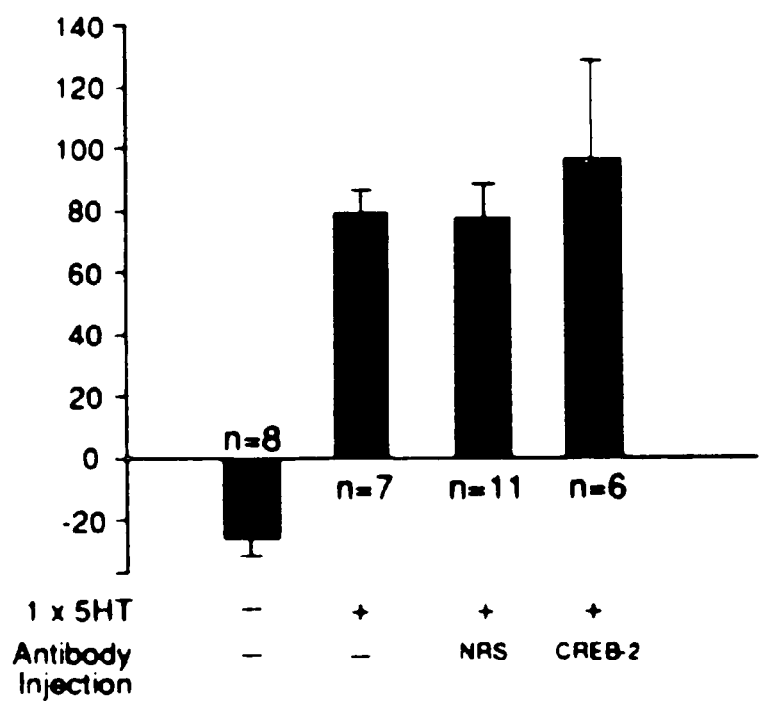

The effect of ApCREB-2 antiserum injection on short-term facilitation induced by one pulse of 5-HT was next investigated. One minute after exposure of one pulse of 5-HT the noninjected cells showed a facilitation of +79.43% (±7.06, n=7), the ApCREB-2 antiserum injected cells showed a facilitation of +96.17% (±32.35, n=6) and the cells injected with normal rabbit serum had a facilitation of +76.45% (±12.03, n=11) (FIG. 8D). All these values are significantly different from the decrease in EPSP amplitude due to homosynaptic depression observed in non-5-HT-treated control cells (−25.5%±5.59, n=8, p<0.01). Thus, as with other agents that specifically affect the long-term process, ApCREB-2 antiserum has no effect on the short-term process.

One Pulse of 5-HT Paired with Injection of the ApCREB-2 Antiserum Induces the Growth of New Synaptic Connections Long-term memory for sensitization of the gill-withdrawal reflex is associated with the growth of new synaptic connections between the sensory neurons and their follower motor neurons (Bailey and Chen, 1983, 1988). The duration of this structural change parallels the behavioral retention of the memory (Bailey and Chen, 1989). Similar changes can be observed in sensory-motor neuron cocultures where five pulses of 5-HT produce a long-lasting (24 hr) increase in the number of sensory varicosities contacting the motor neuron (Glanzman et al., 1990; Bailey et al, 1992).

To determine whether ApCREB-2 can also act as a repressor of the morphological changes that accompany long-term facilitation, the ApCREB-2 antiserum was injected into sensory neurons and examined the consequences of one pulse of 5-HT on long-term changes in both the strength of the sensory-motor neuron connection and on the number of fluorescently-labeled sensory neuron varicosities contacting the motor neuron (FIGS. 9 and 10). The pairing of a single pulse of 5-HT with the injection of ApCREB-2 antiserum 1 hr before training induced significant increases, 24 hr after the injection, in both the strength of the sensory-motor neuron connection (66%±12, n=8, p<0.001), and in the number of sensory neuron varicosities contacting the postsynaptic motor neuron (59%±8, n=8, p<0.001).

By contrast, control cells receiving just one pulse of 5-HT and no injection of antiserum showed no facilitation (−31.5%±6, n=6) and no increase in the number of sensory neuron varicosities (−10%±7, n=6) 24 hr following training (FIG. 9). FIG. 10 contains examples of raw data taken from individual cocultures and illustrates the marked long-term increases in both the amplitude of the evoked EPSP and the number of fluorescently-labeled sensory neuron varicosities elicited by one pulse of 5-HT in the presence of antibody to ApCREB-2. As is the case with the structural changes induced by conventional 5×5-HT long-term training in vitro, the application of one pulse of 5-HT paired with injection of ApCREB-2 antiserum now results in the formation of new sensory neuron varicosities in contact with the motor neuron as well as new neuritic outgrowth. The magnitude of both the long-term functional and structural changes are comparable to those seen at 24 hr following five pulses of 5-HT (Glanzman et al., 1990; Bailey et al., 1992).

Discussion

A bZIP transcription factor, ApCREB-2, has been cloned which is homologous to human CREB-2 Hai et al., 1989; Tsujimoto et al., 1991: Karpinski et al, 1992) and mouse ATF-4 (Mielnicki and Pruitt, 1991; Vallejo et al., 1993). ApCREB-2 represses the activation mediated by ApCREB-1 in mouse F-9 cells. Following injection into the presynaptic sensory neurons of two specific ApCREB-2 antisera, one pulse of 5-HT, which normally induces short-term presynaptic facilitation that does not require RNA or protein synthesis, produces long-term facilitation that lasts more than a day, requires both transcription and translation, and is accompanied by a growth of new synaptic connections.

Although the parallel between the inhibition of ApCREB-1 mediated transactivation in the F9 cells, and the inhibitory action of ApCREB-2 in the sensory neurons, is suggestive, the functional repression by ApCREB-2 in the induction and maintenance of long-term facilitation does not necessarily mean it occurs by means of transcriptional repression. Since ApCREB-2 can activate transcription on its own, it is conceivable that ApCREB-2 may be a repressor only indirectly and that it functions in sensory neurons by activating expression of genes that are themselves inhibitory for the induction of long-term facilitation. Furthermore, the possibility cannot be ruled out that the anti-ApCREB-2 antibodies activate ApCREB-2 rather than blocking it. Nevertheless, the idea that ApCREB-2 acts as a direct repressor of long-term facilitation is favored. The data so far are most consistent with the idea that the anti-ApCREB-2 antibodies prevent ApCREB-2 from interacting with transcriptional activators (such as ApCREB-1).

ApCREB-2 Resembles Human CREB-2 in Both Sequence and Repression of ApCREB-1

ApCREB-2 resembles most closely human CREB-2 and mouse ATF-4 in its primary amino acids sequence and in its binding (albeit with low affinity) to the CRE (Hai et al., 1989; Karpinski et al., 1992). Furthermore, interaction of ApCREB-2 with Ap/CEBP resembles the interaction of ATF-4 and C/EBP (Vallejo et al., 1993). In addition, ApCREB-2 represses ApCREB-1 mediated transactivation in F9 cells, thus resembling the repression of CREB-1 by human CREB-2. (Karpinski et al., 1992, Jungling et al., 1994;). In fact, ApCREB-2 can substitute for human CREB-2 as a repressor of mammalian CREB-1 in mouse F9 cells.

The mechanisms whereby ApCREB-2 mediates transcriptional repression of ApCREB-1 are not yet elucidated. However, its action seems to be distinct from the known inducible and constitutive repressors of CRE-mediated transactivation. For example, unlike the inducible repressors ICER or E4BP4 (Molina et al., 1993, Cowell et al., 1992), ApCREB-2 is constitutively expressed and can act as a transcriptional activator. This ability to activate transcription also distinguished ApCREB-2 from the constitutive repressors of CRE-mediated transactivation exemplified by CREM and ApCREB-2 also lacks other features characteristic of the CREMs, such as the highly conserved KID domain. (Foulkes and Sassone-Corsi, 1992;).

In Addition to being a Repressor of ApCREB-1, ApCREB-2 can Also be an Activator

The finding that ApCREB-2 can both repress and activate transcription further demonstrates that the distinction between activators and repressors is not strict but is critically dependent on the particular promoter, on the recruitment of the specific second messenger pathways, and on the repertoire of the transcription factors available (Hai et al., 1989; Vallejo et al., 1993; Lemaigre et al., 1993;. Ellis et al. 1995). ApCREB-2 is an activator as a GAL4 fusion protein in yeast and a PKA dependent transactivator when cotransfected with the 5xCRE-VIP-lacZ reporter gene. However, ApCREB-2 does not activate transcription from the minimal CRE-SV40 regulatory region in pGL3-CRE reporter gene although it can repress the transactivation by ApCREB-1 from this minimal reporter. The reason for this difference is not clear. Perhaps for effective transactivation, ApCREB-2 requires multiple CRE elements; alternatively, ApCREB-2 may interact with additional regulatory elements in 5xCRE-VIP-lacZ reporter that are unrelated to the CRE.

Induction of Long-Term Memory Requires the Coordinated Regulation of Both CREB-1 and CREB-2

The data herein provide evidence that ApCREB-2 is a functional repressor of long-term facilitation. These data provide the first molecular evidence for a possible role of functional repressors in memory storage. Overexpression of an inhibitory form of Drosophila CREB-1, dCREB-2b, blocks the formation of long-term memory in transgenic flies (Yin et al., 1994). Recently, Yin et al. (1995) demonstrated that overexpressing the activating form of Drosophila CREB-1 (dCREB-2a) greatly reduces the number of training trials needed to establish long-term memory. This gain of function, where a single massed training trial is sufficient to achieve long-term memory which normally requires spaced training trials, greatly strengthens the earlier evidence from Drosophila (Yin et al., 1994, 1995), Aplysia (Dash et al., 1990; Kaang et al., 1993), and mice (Bourtchuladze et al., 1994) that CREB-1 is of central importance in initiating the long-term memory formation.

The results in Aplysia point to a parallel importance for ApCREB-2 in this process. Injection of anti-ApCREB-2 antibodies paired with a single training trial, which normally produces only short-term facilitation, results in induction of long-term facilitation. This gain of function resembles overexpression of the dCREB-2a activator in Drosophila. These findings suggest the interesting possibility that removal of the ApCREB-2-mediated repression may be limiting in regulating the long-term increase in synaptic strength.

A Possible Mechanism for the Physiological Role of ApCREB-2

There are a number of ways by which a transcription factor such as ApCREB-2 could directly repress (for recent review, see Johnson, 1995). First, ApCREB-2 could act directly to inhibit the basal transcriptional machinery. Since ApCREB-2 can be an activator on its own, this is unlikely. Second, ApCREB-2 could compete for the DNA binding sequence with ApCREB-1 (or another activator). Since the affinity of the ApCREB-2 homodimers for CRE is much lower than that of ApCREB-1, this is also unlikely. Therefore, the possibility that ApCREB-2 might mediate repression by interacting directly with ApCREB-1 (or another activators) to form an inactive heterodimer is favored. Both ApCREB-1 and ApCREB-2 are coexpressed in the sensory neurons. Moreover, ApCREB-2 can form heterodimers on a CRE with rat CREB-1 in vitro. However it remains to be determined whether ApCREB-2 also heterodimerizes with ApCREB-1 in vivo.

How might the repression of ApCREB-1 by ApCREB-2 be relieved? Since a change in the amount of the ApCREB-2 protein after exposure to 5-HT is not detected, the relief of repression most likely does not involve targeted degradation of the ApCREB-2 protein. More likely the repressive action of ApCREB-2 is relieved by a covalent modification induced by the repeated pulses of 5-HT. According to this view, the physiological role of ApCREB-2 may be:

First it may prevent the long-term process from being turned on adventitiously without repeated exposures to 5-HT.

Second, it may regulate the amplitude of synaptic change by integrating the activation of ApCREB-1 by PKA with signals from additional second messenger pathways. The induction of long-term facilitation and the concomitant structural changes induced by a single pulse of 5-HT paired with injection of anti ApCREB-2 antibody is consistent with the idea that a single pulse of 5-HT is sufficient to fully induce the activating pathway. The finding that ApCREB-2 transcriptionally represses ApCREB-1 in the presence of cotransfected catalytic subunit of PKA in F9 cells indicates that another pathway besides PKA (a pathway not active in undifferentiated F9 cells) must mediate its derepression. This suggests the interesting possibility that additional second messengers and kinases or phosphatases may be involved in relieving the repression.

The pathways regulating stimulation of the activator and relief of the repressor may have distinctive kinetics. Such differences in kinetics could define the optimal time window separating training trials and account for the well established difference between massed and spaced training. In cell culture, as in the intact animal, spaced training (5 pulses of 5-HT separated by 20 min) trial is more effective in triggering long-term facilitation than massed training (5 pulses of 5-HT not separated at all but given continuously over 25 min). The synaptic potential is facilitated by +80% (12.95, n=15) after 5 spaced pulses as compared with only +39% (19, n=16) after 25 minutes of continuous exposure to 5-HT. Perhaps the reason that spaced training is more effective than massed training is that only spaced training allows coordinated activation of ApCREB-1 and derepression of ApCREB-2.

That 5-HT triggers different signaling pathways in a coordinated way PKA to stimulate the activator and possibly others to relieve the repressor should not be taken to indicate that each of these pathways cannot be engaged alone by other transmitter signals acting on surface receptors. Certain modulatory transmitters might act selectively to relieve repression. Such a priming action on memory might allow for one trial learning.

One Trial Learning: Flashbulb Memories

Dual control of activators and repressors by different second messenger pathways could provide a beginning insight into to a range of features characteristic of memory, ranging from amnesia to photographic memory. For example, a characteristic feature of age-related memory loss (benign senescent forgetfulness) is the inability to consolidate long-term memories (Petersen et al., 1992). This aging defect, therefore, may represent not only a weakening stimulation by activators, but perhaps also an inability to relieve repression. Conversely, genetically endowed differences in the activity of the repressor in relation to the activator could prime the storage process and contribute to exceptional memory. Although long-term memory typically requires repeated spaced training, it occasionally occurs following a single exposure. One trial learning is particularly well-developed in certain rare individuals (memorists) with exceptional memory. For example, the famous memorist D. C. Shershevski, studied by A. R. Luria (1968), seemed never to forget anything he had learned following a single exposure, even after more than a decade. More commonly, memorists have more restricted capabilities: they may be exceptionally good in remembering certain specific types of knowledge and not others (Brown and Deffenbacher, 1995). There are people with astonishing memory that is selective for visual images, for musical scores, for chess games, for poetry, or for faces. But photographic memory is not limited to memorists. The most common type of photographic memory, flashbulb memory, is a detailed and vivid memory most people store on one or another occasion and retain for a lifetime (Brown and Kulik, 1977; Conway, 1995; Neisser, 1982). Flashbulb memories, such as the memory of where you were when President Kennedy was assassinated, preserve knowledge of an event in an almost indiscriminate way, much as a photograph preserves all the details of the scene. Initial studies on flashbulb memories focused on important historical events. But there is now good evidence that autobiographical details of surprising and important defining personal events are retained with the same vivid clarity for details (Conway, 1995).

How are the details of these dramatically personal and historical events stored? These surprising and emotionally-charged events are thought to recruit the amygdala and the major arousal systems of the brain the serotonergic, noradrenergic, dopaminergic, and cholinergic modulatory systems (McGaugh et al., 1993). One potential consequence of the action of these modulatory systems might be to relieve repression and thereby prime the memory system. It is therefore of particular interest that these modulatory systems can play a significant role in the CREB-related learning in *Aplysia, Drosophila*, and mice.

EXPERIMENTAL PROCEDURES

General Methods

Standard manipulations of *E. coli, S. cerevisiae*, proteins and nucleic acids, were performed essentially as described in Maniatis et al. (1989), Ausubel et al., (1994) and Harlow and Lane (1988).

Plasmids and Cloning

Cloning was generally done by PCR using Ultima DNA polymerase (Perkin Elmer). The *Aplysia* CNS specific cDNA library was constructed in pGAD10 and the ApC/EBP bZIP domain (amino acids 151–286) was cloned in pMA424 (Ma and Ptashne, 1987). Subsequent subcloning was carried out in pAS1 and pACT2 plasmids (Durfee et al., 1993). The initiation codons of ApCREB-2, ApC/EBP and ApCREB-1 were replaced by an NcoI restriction site by PCR and cloned in the NcoI-SacI site of pGEX-KG (Guan and Dixon, 1991) or pET-30 (Novagen, modified by replacing the NdeI-NcoI fragment by a synthetic oligonucleotide encoding the initiating methionine followed by six histidines). The mammalian expression constructs pRcRSV-ApCREB-2 and pRcRSV-ApCREB-1 were made by subcloning the corresponding cDNAs in pRcRSV (Invitrogen). The reporter pGL3-CRE was made by cloning a single CRE palindrome into a pGL3 promoter luciferase reporter plasmid (Promega). The plasmids pRcRSV-PKA C-α1 expressing the PKA catalytic subunit and pRcRSV-CREB341 expressing the wild type rat CREB were utilized.

Aplysia CNS cDNA Library Construction, Two-Hybrid Screening in Yeast and GAL4 DNA Binding Domain Activation Assay The Aplysia CNS cDNA library was synthesized in pGAD10 using random hexamers and the BRL cDNA synthesis kit. Two libraries constructed from size fractionated cDNAs with average inserts >2 kb ($5 \times 10^6$ independent clones each) were used in the two-hybrid screening as described previously (Fields and Song., 1989, Durfee et al., 1993, Ausubel et al., 1994). The transcriptional activation properties of ApCREB-2 and its interaction with other proteins in the two-hybrid system was analyzed using the full length ApCREB-2 and its deletion mutants subcloned in pAS1 and pACT2 vectors. The transcriptional activity of ApCREB-2/GAL4 DNA binding domain fusions was determined as decribed (Ma and Ptashne, 1987; Durfee et al., 1993). To analyze the protein interactions, ApCREB-2, ApC/EBP, rat CREB, c-fos and deletion mutants of these proteins in pAS1 and pACT2 were cotransformed into S. cerevisiae Y190, and the expressed β-galactosidase quantified as above.

Purification of Recombinant Proteins

The induction and purification of GST fusion proteins were done as described (Frangioni and Neel, 1993). 6His-ApCREB-2 fusion protein was expressed and purified using the QIAexpress system (Qiagen, denaturing protocol). The bound 6His-ApCREB-2 protein was renatured on the Ni-NTA resin and eluted with 250 mM imidazole.

Antisera Production, Depletion and Affinity Purification

Two rabbit antisera were raised (BABCO) against GST-ApCREB-2 and one against GST-ApC/EBP fusion proteins. The anti-ApCREB-2 antisera were depleted of ApCREB-2 specific antibodies by incubation with an equal volume of glutathione-agarose saturated (3 μg/μl) with GST-ApCREB-2 fusion protein. The matching controls for Western blots and electrophysiological experiments were prepared by parallel incubation of the immune antisera with glutathione-agarose saturated with GST. The antibodies were affinity purified on the GST-ApCREB-2, GST-ApC/EBP proteins coupled to Affi Gel (Bio Rad). Prior to purification, the antisera were peadsorbed on the GST-Affigel.

Western Blotting

20 μg of Aplysia CNS extract were separated on 10% SDS-PAGE, electroblotted to PVDF membranes (Immobilon-P, Millipore) The membranes were probed with affinity purified anti-ApCREB-2, anti-ApC/EBP antibodies or anti rat CREB antiserum (UBI) followed by anti-rabbit-HRP and visualized by chemiluminescence (ECL, Amersham).

Immunoprecipitation

The CNS ganglia removed from anesthetized Aplysia were labeled with $^{35}$S-methionine, overnight at 18° C., homogenized in 10 mM Tris pH 7.2, 350 mM NaCl, 0.5% Triton X-100, 50 mM β-glycerophosphate, 25 mM NaF, 1 mM NaVO$_4$, 2 mM DTT, 1 mM PMSF, 5 mM benzamidine and 10 μg/ml each of chymostatin, leupeptin, antipain and pepstatin A. After diluting 1:1 with 2×RIPA, the extract was precleared with Protien A-Sepharose for 1 hr at 4° C., incubated with affinity purified anti-ApCREB-2 antibody for 1 hr at 4° C. followed by Protein A Sepharose (Pharmacia). The immunoprecipitated proteins were resolved by 10% SDS-PAGE, and visualized by fluorography (Amplify, Amersham).

Phosphatase Treatment of Aplysia CNS Extracts

Both phosphatase and mock buffer cocktails contained 20 mM MgCl$_2$, 0.5 mM EGTA, 1 mM PMSF, 5 mM benzamidine and 10 (g/ml each of chymostatin, leupeptin, antipain and pepstatin A. The phosphatase mix contained 2 U of calf intestinal phosphatase, the mock mix 20 mM NaF and 20 mM β-glycerophosphate. These cocktails were added to 40 μg of the CNS extracts and incubated at 37° C. for 30 min. The reactions was stopped by the addition of SDS sample buffer and the proteins were visualized by Western Blotting with affinity purified anti-ApCREB-2 antibodies.

RNA Extraction from Sensory Neuron Cultures and RT-PCR

Cultures of approximately 200 Aplysia sensory neurons, established by the dissociation of the pleural sensory cluster in a single dish, were exposed to 10 μM 5-HT for 5 min once or five times separated by 20 min. After washing with ASW, cells were lysed by 100 μl of the guanidium thiocyanate solution and the RNA was isolated. For RT-PCR, the isolated RNA was treated with RNAse free DNAse (Boehringer), reextracted as above and processed using RT-PCR kit (Boehringer). The sequence of the primers used were TTC-CGCTTTCCATAAGTCGA (Seq ID No 6) and ACCT-GAAAATGATATTGTAC (Seq ID No 7).

DNA Binding Site Selection

Optimal recognition sequences for DNA binding of ApCREB-2 and ApC/EBP were determined by a PCR assisted binding site selection method (Norby et al. (1992). The oligonucleotides which bound in 150 mM KCl (standard isotonic condition) or 400 mM KCl (resembling Aplysia cell osmolarity) were eluted by 1M KCl, diluted and PCR amplified. After 13 cycles of binding and PCR amplification the amplified products were cloned in Bluescript (Stratagene) and sequenced. In each of the 48 independent clones from both the low and high salt conditions the BS1 binding sequence (for ApCREB-2) or BS2 (for ApC/EBP) was present.

In Vitro Protein Binding Assay $^{35}$S methionine-labeled ApCREB-2 and ApC/EBP were translated in the TNT rabbit reticulocyte lysate (Promega). Ten μl of the lysates containing the in vitro translated proteins were mixed with 25 μl of Glutathione-Sepharose beads saturated with Glutathione S-transferase (GST) or GST fusion proteins in 400 μl of PBS and mixed for 1 hour at room temperature. The bound complexes were washed thoroughly with 20 ml of 0.1% Triton X-100 in PBS on a minicolumn (Wizard, Promega), eluted in SDS sample buffer and resolved by 10% SDS-PAGE.

Electrophoretic DNA Mobility Shift Assays (EMSA)

The sequences listed show one strand of the double stranded oligonucleotides used in the gel mobility shift assays. The sequences in capital letters correspond to: the somatostatin gene CRE (SOM CRE) gatccggcGCCTCCT-TGGCTGACGTCAGAGAGAGAGA (Seq ID No 8), the palindromic core CRE (CRE) gatccggcTGACGTCAt-caagcta (SEQ ID NO 9), the phosphoenolpyruvate carboxykinase gene CRE-1 (PEPCK CRE) gatccCCTTACGTCA-GAGGCGA (SEQ ID NO 10), the enkephalin gene CRE (ENK CRE) gatccggcGCGGGGCTGGCGTAGGGCCT-GCGTCAGCTGCA (SEQ ID NO 11), the ApC/EBP gene putative CRE (Ap CRE) GAGTGGCATCTACGTCAAG-GCTTC (SEQ ID NO 12), the ApCREB-2 DNA binding sequence (BS1 CRE) gatccggcAGTATTGCGTCATCt-caagcta (SEQ ID NO 13), the composite CRE-CAAT site (CRE-C/EBP) gatccggcTGACGCAATtcaagcta (SEQ ID NO 14), the angiotensin gene acute phase response element (ANG-APRE) gatccACAGTTGTGATTTCACAACCT-GACCAGA (SEQ ID NO 15), the ApC/EBP DNA-binding sequence (BS2 C/EBP) gatccggcACTATTGCGCAATCt-caagcta (SEQ ID NO 16) and the C/EBPβ binding sequence of the c-fos promoter (ERE) gatcCATATTAAGGACAT-GCCG (SEQ ID NO 17).

The EMSA assays were performed as described in Ausubel et al. (1994) using the high ionic strength TGE buffer, 200 ng of recombinant 6His-ApCREB-2, 200 ng of poly (dI-dC) (Pharmacia), and 25 fmol of $^{32}P$ end-labeled double-stranded oligonucleotide probes.

F9 Cell Culture, Transfections and Reporter Gene Assays

Undifferentiated mouse F9 cells were transfected using Lipofectamine (BRL). The β-galactosidase and luciferase activities were quantitated by chemiluminescence (Galacton Plus, Tropix, and a Luciferase assay kit, Promega) in a Turner 20e luminometer.

*Aplysia* Cell Culture and Electrophysiology

*Aplysia* sensory neurons from the pleural ganglia of adult animals (80–100 g) were cocultured with the motor neuron L7 from juvenile animals (0.5–4 g). After 4–5 days in culture, the strength of the synaptic connections between the sensory and motor cell was measured electrophysiologically, as previously described (Montarolo et al. 1986, Alberini et al., 1994). The motor neuron was impaled with a glass microelectrode filled with 2.5M KCl (10 MΩ (resistance) and its membrane potential was held at 30 mV below its resting value. The EPSP was evoked by extracellular stimulation of the sensory neuron and the data were stored on a 4 channel tape recorder.

Induction of Facilitation and Antisera Injection

Two protocols were used to induce synaptic facilitation in *Aplysia* cocultures. In the first, after testing the initial EPSP amplitude, 10 μM 5-HT was applied for 5 min (single pulse). The EPSP was retested 1 min (short-term facilitation), 2 or 24 hr (long-term facilitation) after the washout of the 5-HT. The amount of facilitation was calculated as the percentage change in EPSP amplitude recorded before and at the different time points after the single 5-HT application. In the other group of experiments, long-term facilitation was evoked by five exposures to 10 μM 5-HT for 5 min each, at 20 min intervals (5 pulses). The facilitation was calculated as the percentage change in EPSP amplitude 24 hr after the five pulses of 5-HT. The antisera, adjusted to the osmolarity of *Aplysia* neurons (Alberini et al., 1994), were pressure injected into the sensory neurons 1 hr before 5-HT treatment. Where indicated, anisomycin (10 μM) or actinomycin D (50 μg/ml) was added to the cocultures 1 hr before the 5-HT pulse and was present continuously during the 5-HT treatment. All data are presented as mean percentage change ±SEM in the EPSP amplitude measured after treatment, as compared with its initial pretreatment amplitude. A one way analysis of variance and Newman Keuls multiple range test were used to determine the significance of the EPSP changes.

Dye Injection, Cell Imaging and Quantification of Structural Changes

Individual sensory neuron were cocultivated with a single motor cell. Glass micropipettes were filled with a 6% sterile-filtered solution of the fluorescent dye 5(6)-carboxy-fluorescein (chromatographically purified; Molecular Probes) in 0.44 M KOH (pH 7.0, resistance 50-90 M. The dye was injected into the sensory neurons immediately after measuring the initial EPSP amplitude by 0.4–0.6 nA hyperpolarizing current pulses (500 ms duration at 1 Hz) for 4–6 min, phase contrast and fluorescence images of the same view areas were taken both before and 24 hr after treatment as previously described (Glanzman et al., 1990; Bailey et al., 1992).

Varicosities were identified according to criteria previously established for sensory neurons in vivo (Bailey et al., 1979; Bailey and Chen, 1983, 1988), and in vitro (Glanzman et al., 1990; Bailey et al., 1992) and included all slightly elongated spheres of approximately 2–3 μm or more in diameter.

SEQUENCES

Accession Number 1123036

Definition: *Aplysia* californica bZIP transcription factor (ApCREB2) mRNA, complete cds.

GenBank Name: ACU40851, Accession: U40851 NCB Seq ID: 1123036

Citation D Bartsch, M Ghirardi, P Skehel, K Karl, S Herder, M Chen, C Bailey & E Kandel (1995). *Aplysia* CREB2 represses long-term facilitation: relief of repression converts transient facilitation into long-term functional and structural change.

Cell 83, 979–992. MEDLINE identifier: 96107336

Coding region function: bZIP transcription 1123036: 190..1326 factor; repressor.

Sequence    1336 nt, linear rna
  1 acgctacaga acggtcaaga aatataatgt gtgcaaagat gtctgcttag   (SEQ ID NO 18)

51 gaagacacgg cgacgtccgc ccccaagggc aatcggcaca atggcaacct 101 ttcatgatgt attcctagct acggctatct cgcttctcta ttggacggat 151 ttatttatca catagaagac tcgtatacca aactctacga tggagctgga 201 cctttggagc gaagattttc aactggccag ggaatggggg ctggaaatgc 251 cagtcgtcca gaccgatggc cagttcggtg acctcaaatc aaccagtcgt 301 catggtggcg acgaatctct aagtttgcag ccccagggcg ctacactgaa 351 gttggaaccc tttgaggaag atgtccttgg tgcagagtgg atggagtcgt 401 ccgatctcgg ctcttttctg gatgctttgg gtgacaacca tgagcggctg 451 catccgttcg agtcaaactt gctcgagttc acttctctga tcactcctga 501 tgattcgacg gtgtcaaagg acattctcag ctcaactctt cagtttccaa 551 ctcaaccagt gaacatccct ttatatgcaa gtcatgggc cgaagatttc 601 tctgcagaga ctgagtttga gaaccacctg tcgcctccag attctccgga 651 gcaggtagcc cctgtcataa atctagaacc agttgaactc actgcgagcc 701 atatgacggt gatctcacct gatggcttgt tgggtggcat ggaactggct 751 tcagaaagct taacatttac cgaactagac tttgtgaact tcaatgacag 801 tgctgttggt tcaattggcg gtgctgaaga acttcttggc tccccactgt 851 cagttgatga tgtggaaagt acaatatcat tttcaggtcc atcgtcgcca 901 gaaaccagcc agagcagcat cattgaatca agtcctgaat tgtacaaagt 951 tatctctacc tcgtccattg atgcatctaa gcgtttctct ccatactctc 1001 gttcctccaa gtccaagcaa tctgtcaaga cttcagacgc taaggcacct 1051 cgtaaaacga ggacaccggc gcagcctgtg ccagaacatg tcatcatgga 1101 acatttggac aaaaaggaca gaaagaagct tcagaacaag aatgctgcca 1151 ttaggtatag gatgaagaag aagggggagg ctcagggcat caaaggggag 1201 gaacaggaat tagaagaact caacacaaag cttaagacta aggtcgatga 1251 cttgcaaaga gaaatcaagt acatgaaaaa tttaatggaa gatgtttgca 1301 aggcgaaagg tattcagctt aaatagtggg aagggt Accession Number 1123037

Definition ApCREB2

Protein Name: ApCREB2 1123037: [Whole]

NCBI Seq ID: 1123037

Citation D Bartsch, M Ghirardi, P Skehel, K Karl, S Herder, M Chen, C Bailey & E Kandel (1995). *Aplysia* CREB2 represses long-term Facilitation: relief of repression converts transient facilitation into long-term functional and structural change.

Cell 83, 979–992.

MEDLINE identifier: 96107336
Citation Data Submission: D. Bartsch (1995).
Coding region function: bZIP transcription 1123036:
190..1326 factor; repressor.

```
Sequence      378 aa
  1 meldlwsedf qlarewglem pvvqtdgqfg dlkstsrhgg deslslqpqg   (SEQ ID NO 1)

51 atlklepfee dvlgaewmes sdlgsfldal gdnherlhpf esnlleftsl 101 itpddstvsk dilsstlqfp tqpvniplya shgaedfsae tefenhlspp 151 dspeqvapvi nlepveltas hmtvispdgl lggmelases ltfteldfvn 201 fndsavgsig gaeellgspl svddvestis fsgpsspets qssiiesspe 251 lykvistssi daskrfspys rsskskqsvk tsdakaprkt rtpaqpvpeh 301 vimehldkkd rkklqnknaa iryrmkkkge aqgikgeeqe leelntklkt 351 kvddlqreik ymknlmedvc kakgiqlk
```

Example 3

CREB2 as a Negative Regulator of Neuronal Growth, Neuronal Differentiation and Neuronal Re-Differentiation The blockage of activity of ApCREB2 by antibody paired with a pulse of 5-HT induces long-term facilitation which is accompanied by growth of new synaptic connections. One view of this process is that 5-HT may be functioning as a growth factor and thus may be capable of the induction of synaptic growth. Since neuronal growth involves the migration of growth cones and the establishment of neuronal connections, the induced synaptic growth may be considered a form of neuronal differentiation as known to be present in the early stages of neuronal development. This process may be considered re-differentiation since it is possible that this growth factor-like activity may occur subsequent to the initial development following a trauma situation. This re-differentiation would rebuild the synaptic connections in order to facilitate the formation of long-term memory. Therefore, CREB2 and its mammalian homologue, ATF4, would be a negative regulator in this process.

The above may be tested in a cellular model of neuronal differentiation, specifically the rat pheochromocytoma cells PC12. The cell line is widely used as a model for neuronal differentiation and also for apoptosis, which is programmed neuronal cell death. PC12 cells are undifferentiated in culture and can be differentiated in vitro by exposing them to nerve growth factor (NGF) and cAMP analogs. Withdrawal of these compounds from the cell culture conditions leads to programmed cell death.

It has been investigated whether ATF4 plays a role in the neuronal differentiation of PC12 cells. It has been demonstrated that in the course of PC12 cellular differentiation, the amount of ATF4 is dramatically reduced (likely by reducing its transcription) in cells exposed to NGF or cAMP analogs. In addition, overexpression of ATF4 in PC12 cells by transfecting expression constructs with constitutive CMV promoter and ATF4 cDNA prevents the PC12 cells from undergoing neuronal differentiation. Taken together, these data support the proposal that the ATF4 gene is a regulator (negative regulator) of neuronal differentiation and that a long term memory acquisition may be a particular form of neuronal differentiation. It is important to also study the role of ATF4 in apoptosis. Since both differentiation and cell death in PC12 cell culture involve similar signal transduction pathways, it is reasonable that ATF4 may be involved in this process as well.

Thus, compounds which are capable of interfering with the binding of a protein or a DNA with a cAMP-response-element-binding-protein- 2 may be useful in memory improvement and also in neuronal regeneration after injury and potentially cell death in several human diseases including stroke and Alzheimer's disease. If ATF4/CREB2 is a negative regulator in neuronal differentiation, compounds or pharmaceutical compositions which target the action of ATF4/CREB2 could improve neuronal regeneration after injury, either alone or in combination with growth factors like NGF. Furthermore, interfering with ATF4 function could slow down damage induced by stroke and maybe some progressive neuronal diseases with extensive cell death, like Parkinson's diseae or Alzheimer's disease.

REFERENCES

Alberini, C., Ghirardi, M., Metz, R., and Kandel, E. R. (1994). C/EBP is an immediate-early gene required for the consolidation of long-term facilitation in *Aplysia. Cell* 76, 1099–1114.

Ausubel, F. M., Brent, R., Kingston, R. E., Moore, D. D., Seidman, J. G., Smith, J. A and Struhl, K. (1994). Current Protocols in Molecular Biology (New York, John Wiley and Sons).

Bacskai, B. J., Hochner, B., Mahaut-Smith, M., Adams, S. R., Kaang, B.-K., Kandel, E. R., and Tsien, R. Y. (1993). Spatially resolved dynamics of cAMP and protein kinase A subunits in *Aplysia* sensory neurons. *Science* 260, 222-226.

Bailey, C. H., and Chen, M. (1983). Morphological basis of long-term habituation and sensitization in *Aplysia. Science* 220, 91-93.

Bailey, C. H. and Chen, M. (1988). Long-term memory in *Aplysia* modulates the total number of varicosities of singe identified sensory neurons. *Proc. Natl. Acad. Sci. USA* 85, 2373-2377.

Bailey, C. H. and Chen, M. (1989). Time course of structural changes at identified sensory neuron synapses during long-term sensitization in *Aplysia. J. Neurosci.* 9, 1774-1780.

Bailey, C. H., Montarolo, P., Chen, M., Kandel, E. R., and Schacher, S. (1992). Inhibitors of protein and RNA synthesis block structural changes that accompany long-term heterosynaptic plasticity in *Aplysia. Neuron* 9, 749-758.

Bailey, C. H., and Kandel, E. R. (1993). Structural changes accompanying memory storage. *Annu. Rev. Physiol.* 55, 397–426.

Bailey, C. H., Thompson, E. B., Castellucci, V. F., and Kandel, E. R. (1979). Ultrastructure of the synapses of sensory neurons that mediate the gill-withdrawal reflex in *Aplysia. J. Neurocytol.* 8, 415-444.

Bernier, L., Castellucci, V. F., Kandel, E. R., and Schwartz, J. H. (1982). Facilitatory transmitter causes a selective and prolonged increase in adenosine 3':5'-monophosphate in sensory neurons mediating the gill and siphon withdrawal reflex in *Aplysia. J. Neurosci.* 2, 1682-1691.

Bourtchuladze, R., Frenguelli, B., Blendy, J., Cioffi, D., Schutz, G., and Silva, A. J. (1994). Deficient long-term memory in mice with a targeted mutation of the cAMP responsive element-binding protein. *Cell* 79, 59-68.

Brown, E., and Deffenbacher, K. (1995). Forgotten mnemonists. *J. Hist. Behav. Sci.* 11, 342-349.

Brown, R., and Kulik, J. (1977). Flashbulb memories. *Cognition* 5, 73-99.

Brunelli, M., Castellucci, V., and Kandel, E. R. (1976). Synaptic facilitation and behavioral sensitization in *Aplysia*: Possible role of serotonin and cyclic AMP. *Science* 194, 1178-1181.

Carew, T. J., Castellucci, V. F., and Kandel, E. R. (1971). An analysis of dishabituation and sensitization of the gill-withdrawal reflex in *Aplysia. Int. J. Neurosci.* 2, 79–98.

Carew, T. J., Pinsker, H. M., and Kandel, E. R. (1972). Long-term habituation of a defensive withdrawal reflex in *Aplysia. Science* 175, 451-454.

Castellucci, V. F., Blumenfeld, H., Goelet, P., and Kandel, E. R. (1989). Inhibitor of protein synthesis blocks long-term behavioral sensitization in the isolated gill-withdrawal reflex of *Aplysia. J. Neurobiol.* 20, 1-9.

Chevray, P. M., and Nathans, D. (1992). Protein interaction cloning in yeast: Identification of mammalian proteins that react with the leucine zipper of Jun. *Proc. Natl. Acad. Sci. USA* 89, 5789–5793.

Chien, C. T., Bartel, P. L., Sternglanz, and Fields, S. (1991). The two-hybrid system: A method to identify and clone genes for proteins that interact with a protein of interest. *Proc. Natl. Acad. Sci.* 88, 9578-9582.

Conway, M. (1995). Flashbulb Memories (Hillsdale, N. J., Erlbaum).

Cowell, I. G., Skinner, A., and Hurst, H. C. (1992). Transcriptional repression by a novel member of the bZIP family of transcription factors. *Mol. Cell Biol.* 12, 3070-3077.

Dash, P. K., Hochner, B., and Kandel, E. R. (1990). Injection of cAMP-responsive element into the nucleus of *Aplysia* sensory neurons blocks long-term facilitation. *Nature* 345, 718-721.

Davis, H. P., and Squire, L. R. (1984). Protein synthesis and memory: A review. *Psychol. Bull.* 96. 518–559.

Durfee, T., Becherer, K., Chen, P.-L., Yeh, S.-H., Yang, Y., Kilburn, A. E., Lee, W.-H., and Elledge, S. J. (1993). The retinoblastoma protein associates with the protein phosphatase type 1 catalytic subunit. *Genes Dev.* 7, 555–569.

Ellis, M. J., Lindon, A. C., Flint, K. J., Jones, N. C., and Goodbourn, S. (1995) Activating transcription factor-1 is a specific antagonist of the cyclic adenosine 3'.5'-monophosphate (cAMP) response element-binding protein-1-mediated response to cAMP. *Mol Endocrinol* 9:255–265.

Fields, S., and Song, 0. K. (1989). A novel genetic system to detect protein-protein interactions. *Nature* 340, 245–246.

Flexner, J. B., Flexner, L. B., and Stellar, E. (1963). Memory in mice as affected by intracerebral puromycin. *Science* 141, 57-59.

Foulkes, N., and Sassone-Corsi, P. (1992). More is better; Activators and repressors from the same gene. *Cell* 68, 411–414.

Frangioni, J. V., and Neel, B. G. (1993). Solubilization and purification of enzymatically active glutathione S-transferase (pGEX) fusion proteins. *Analytical Biochemistry* 210, 179–187.

Ghirardi, M., Braha, O., Hochner, B., Montarolo, P. G., Kandel, E. R., and Dale, N. (1992). Roles of PKA and PKC in facilitation of evoked and spontaneous transmitter release at depressed and nondepressed synapses in *Aplysia* sensory neurons. *Neuron* 9, 479–489.

Ghirardi, M., Montarolo, P. G., and Kandel, E. R. (1995). A novel intermediate stage in the transition between short- and long-term facilitation in the sensory-to-motor neuron synapse of *Aplysia. Neuron* 14, 413–420.

Glanzman, D. L., Kandel, E. R., and Schacher, S. (1990). Target-dependent structural changes accompanying long-term synaptic facilitation in *Aplysia* neurons. *Science* 249, 799–802.

Guan, K. -L., and Dixon, J. E. (1991). Eukaryotic proteins expressed in *Escherichia coli*: An improved thrombin cleavage and purification procedure of fusion proteins with glutathione S-transferase. *Analyt. Biochem.* 192, 262–267.

Hai, T. W., Liu, F., Coukos, W. J., and Green, M. R. (1989). Transcription factor ATF cDNA clones: An extensive family of leucine zipper proteins able to selectively form DNA binding heterodimers. *Genes Dev.* 3, 2083–2090.

Harlow, E., and Lane, D. (eds.) (1988). Antibodies. (Cold Spring Harbor, N.Y., Cold Spring Harbor Press).

Johnson, A. D. (1995). The price of repression. *Cell* 81, 655–658.

Jungling, S., Cibelli, G., Czardybon, M., Gerdes, H. H., and Thiel, G. (1994). Differential regulation of chromogranin B and synapsin I gene promoter activity by cAMP and cAMP-dependent protein kinase. *Eur. J. Biochem.* 226, 925–935.

Kaang, B.-K., Kandel, E. R., and Grant, S. G. N. (1993). Activation of cAMP-responsive genes by stimuli that produce long-term facilitation in *Aplysia* sensory neurons. *Neuron* 10, 427–435.

Karpinski, B. A., Morle, G. D., Huggenvik, J., Uhler, M. D., and Leiden, J. M. (1992). Molecular cloning of human CREB-2: An ATF/CREB transcription factor that can negatively regulate transcription from the cAMP response element. *Proc. Natl. Acad. Sci. USA* 89, 4820–4824.

Landschulz, W. H., Johnson, P. F., and McKnight, S. L. (1988). The leucine zipper: A hypothetical structure common to a new class of DNA binding proteins. *Science* 240, 1759–1764.

Lemaigre, F. P., Ace. C. I., and Green, M. R. (1993). The cAMP response element binding protein, CREB, is a potent inhibitor of diverse transcriptional activators. *Nucleic Acids Res.* 21, 2907–2911.

Luria, A. R. (1968). The Mind of a Mnemonist (London, Basic Books).

Ma, J., and Ptashne, M. (1987). A new class of yeast transcriptional activators. *Cell* 51, 113–119.

Maniatis, T., Sambrook, Z., and Fritsch, E. F. (1989). Molecular Cloning. (Cold Spring Harbor, N.Y., Cold Spring Harbor Press).

McGaugh, J., Introini-Collison, Il, Cahill, L., Castellano, C., Dalmaz, C., Parent, M., and Williams, C. (1993). Neuromodulatory systems and memory storage: Role of the amygdala. *Behav. Brain Res.* 58, 81–90.

Mielnicki, L. M., and Pruitt, S. C. (1991). Isolation and nucleotide sequence of a murine cDNA homologous to human activating transcription factor 4. *Nucleic Acids Res.* 19, 6332.

Molina, C. A., Foulkes, N. S., Lalli, E., and Sassone-Corsi, P. (1993). Inducibility and negative autoregulation of CREM: An alternative promoter directs the expression of ICER, an early response repressor. *Cell* 75, 875–886.

Montarolo, P. G., Goelet, P., Castellucci, V. F., Morgan, J., Kandel, E. R., and Schacher, S. (1986). A critical period for macromolecular synthesis in long-term heterosynaptic facilitation in *Aplysia. Science* 234, 1249–1254.

Neisser, V. (1982). Snapshots or benchmarks? In Memory Observed: Remembering in Natural Contexts, V. Neisser, ed. (San Francisco, Freeman), pp. 43–48.

Norby, P. L., Pallisgaard, N., Pedersen, F. S., and Jorgensen, P. (1992). Determination of recognition-sequences for DNA-binding proteins by a polymerase chain reaction assisted binding site selection method (BSS) using nitrocellulose immobilized DNA binding protein. *Nucleic Acids Res.* 20, 6317–6321.

Petersen, R., Smith, G., Kokmen, E., Ivnik, R., and Tangalos, E. (1992). Memory function in normal aging. *Neurology* 42, 396–401.

Petrij, F., Giles, R. H., Dauwerse, H. G., Saris, J. J., Hennekam, R. C. M., Masuno, M., Tommerup, N., Van Ommen, G. J. B., Goodman, R. H., Peters, D. J. M., and Bruening, M. H. (1995). Rubinstein-Taybi syndrome caused by mutations in the transcriptional co-activator CBP. *Nature* 376, 348–351.

Pinsker, H., Kupfermann, I., Castellucci, V., and Kandel, E. R. (1970). Habituation and dishabituation of the gill-withdrawal reflex in *Aplysia. Science* 167, 1740–1742.

Pinsker, H. M., Hening, W. A., Carew, T. J., and Kandel, E. R. (1973). Long-term sensitization of a defensive withdrawal reflex in *Aplysia. Science* 182, 1039–1042.

Rayport, S. G., and Schacher, S. (1986). Synaptic plasticity in vitro: Cell culture of identified neurons mediating short-term habituation and sensitization. *J. Neurosci.* 6, 759–763.

Schacher, S., Castellucci, V. F., and Kandel, E. R. (1988). cAMP evokes long-term facilitation in *Aplysia* sensory neurons that requires new protein synthesis. *Science* 240, 1667–1669.

Scholz, K. P., and Byrne, J. H. (1988). Intracellular injection of cyclic AMP induces a long-term reduction of neuronal potassium currents. *Science* 240, 1664–1667.

Skehel, P. A., and Bartsch, D. (1994). Characterization of a Y-box factor from *Aplysia* californica. *Gene* 145, 231–235.

Tsujimoto, A., Nyunoya, H., Morita, T., Sato, T., and Shimotohno, K. (1991). Isolation of cDNAs for DNA-binding proteins which specifically bind to a tax-responsive enhancer element in the long terminal repeat of human T-cell leukemia virus type I. *J. Virol.* 65, 1420–1426.

Vallejo, M., Ron, D., Miller, C. P., and Habener, J. F. (1993). C/ATF, a member of the activating transcription factor family of DNA-binding proteins, dimerizes with CAAT/enhancer-binding proteins and directs their binding to cAMP response elements. *Proc. Natl. Acad. Sci. USA* 90, 4679–4683.

Vinson, C. R., Hai, T., and Boyd, S. M. (1993). Dimerization specificity of the leucine zipper-containing bZIP motif on DNA binding; Prediction and rational design. *Genes Dev.* 7, 1047–1058.

Vinson, C. R., Sigler, B., and McKnight, S. L. (1989). Scissors-grip model for DNA recognition by a family of leucine zipper proteins. *Science* 246, 911–916.

Yin, J. C. P., Del Vecchio, M., Zhou, H., and Tully, T. (1995). CREB as a memory modulator: Induced expression of a dCREB2 activator isoform enhances long-term memory in *Drosophila. Cell* 81, 107–115.

Yin, J. C. P., Wallach, J. S., Del Vecchio, M., Wilder, E. L., Zhou, H., Quinn, W. G., and Tully, T. (1994). Induction of a dominant negative CREB transgene specifically blocks long-term memory in *Drosophila. Cell* 79, 49–58.

---

What is claimed is:

1. A method for enhancing long-term memory in a subject, which comprises administering to the subject a compound that inhibits binding of (i) a cAMP-responsive-element-binding-protein-2 having an amino acid sequence identical to the sequence set forth in SEQ ID NO:1 to (ii) a transcription factor protein and/or DNA, wherein the protein or DNA is an activator of cAMP-responsive gene expression, and wherein the compound is administered in an amount effective to enhance long-term memory in the subject.

2. The method of claim 1, wherein the compound is capable of altering phosphorylation of the cAMP-response-element-binding-protein-2.

3. The method of claim 1, wherein the compound is an organic compound, a peptide, a peptide mimetic, or a nucleic acid.

4. The method of claim 1, wherein the transcription factor protein is a cAMP-response-element-binding-protein, a C/EBP protein, an AF-1 protein, a c-jun protein, or a c-Fos protein.

5. The method of claim is 1, wherein the administration is via intralesional, intramuscular or intravenous injection; infusion; liposome mediated delivery; viral infection; topical, nasal, oral, anal, ocular, cerebro-spinal, or otic delivery.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 379 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Met Glu Leu Asp Leu Trp Ser Glu Asp Phe Gln Leu Ala Arg Glu Trp
1               5                   10                  15

Gly Leu Glu Met Pro Val Val Gln Thr Asp Gly Gln Phe Gly Asp Leu
            20                  25                  30

Lys Ser Thr Ser Arg His Gly Gly Asp Glu Ser Leu Ser Leu Gln Pro
        35                  40                  45

-continued

```
Gln Gly Ala Thr Leu Lys Leu Glu Pro Phe Glu Asp Val Leu Gly
 50                  55                  60
Ala Glu Trp Met Glu Ser Ser Asp Leu Gly Ser Phe Leu Asp Ala Leu
 65                  70                  75                  80
Gly Asp Asn His Glu Arg Leu His Pro Phe Glu Ser Asn Leu Leu Glu
                 85                  90                  95
Phe Thr Ser Leu Ile Thr Pro Asp Asp Ser Thr Val Ser Lys Asp Ile
                100                 105                 110
Leu Ser Ser Thr Leu Gln Phe Pro Thr Gln Pro Val Asn Ile Pro Leu
                115                 120                 125
Tyr Ala Ser His Gly Ala Glu Asp Phe Ser Ala Glu Thr Glu Phe Glu
130                 135                 140
Asn His Leu Ser Pro Pro Asp Ser Pro Glu Gln Val Ala Pro Val Ile
145                 150                 155                 160
Asn Leu Glu Pro Val Glu Leu Thr Ala Ser His Met Thr Val Ile Ser
                165                 170                 175
Pro Asp Gly Leu Leu Gly Gly Met Glu Leu Ala Ser Glu Ser Leu Thr
                180                 185                 190
Phe Thr Glu Leu Asp Phe Val Asn Phe Asn Asp Ser Ala Val Gly Ser
                195                 200                 205
Ile Gly Gly Ala Glu Glu Leu Leu Gly Ser Pro Leu Ser Val Asp Asp
210                 215                 220
Val Glu Ser Thr Ile Ser Phe Ser Gly Pro Ser Ser Pro Glu Thr Ser
225                 230                 235                 240
Gln Ser Ser Ile Ile Glu Ser Ser Pro Glu Leu Tyr Lys Val Ile Ser
                245                 250                 255
Thr Ser Ser Ile Asp Ala Ser Lys Arg Phe Ser Pro Tyr Ser Arg Ser
                260                 265                 270
Ser Lys Ser Lys Gln Ser Val Lys Thr Ser Asp Ala Lys Ala Pro Arg
                275                 280                 285
Lys Thr Arg Thr Pro Ala Gln Pro Val Pro Glu His Val Ile Met Glu
290                 295                 300
His Leu Asp Lys Lys Asp Arg Lys Lys Leu Gln Asn Lys Asn Ala Ala
305                 310                 315                 320
Ile Arg Tyr Arg Met Lys Lys Lys Gly Glu Ala Gln Gly Ile Lys Gly
                325                 330                 335
Glu Glu Gln Glu Leu Glu Glu Leu Asn Thr Lys Leu Lys Thr Lys Val
                340                 345                 350
Asp Asp Leu Gln Arg Glu Ile Lys Tyr Met Lys Asn Leu Met Glu Asp
                355                 360                 365
Val Cys Lys Ala Lys Gly Ile Gln Leu Lys Met
370                 375
```

(2) INFORMATION FOR SEQ ID NO:2:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Leu Asp Lys Lys Asp Arg Lys Lys Leu Gln Asn Lys Asn Ala Ala Ile
 1               5                  10                  15
```

```
Arg Tyr Arg Met Lys Lys Gly Glu Ala Gln Gly Ile Lys Gly Glu
             20                  25                  30

Glu Gln Glu Leu Glu Glu Leu Asn Thr Lys Leu Lys Thr Lys Val Asp
         35                  40                  45

Asp Leu Gln Arg Glu Ile Lys Tyr Met Lys Asn Leu Met Glu Asp Val
     50                  55                  60

Cys Lys Ala Lys Gly Ile Gln Leu Lys
65                  70
```

(2) INFORMATION FOR SEQ ID NO:3:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGACGTCA                                                                              8

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGTATTGCGT CATC                                                   14

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACTATTGCGC AATC                                                   14

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TTCCGCTTTC CATAAGTCGA                                       20

(2) INFORMATION FOR SEQ ID NO:7:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:7:

ACCTGAAAAT GATATTGTAC                                          20

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GATCCGGCGC CTCCTTGGCT GACGTCAGAG AGAGAGA                       37

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GATCCGGCTG ACGTCATCAA GCTA                                     24

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GATCCCCTTA CGTCAGAGGC GA                                       22

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATCCGGCGC GGGGCTGGCG TAGGGCCTGC GTCAGCTGCA                    40

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:12:

GAGTGGCATC TACGTCAAGG CTTC                                    24

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GATCCGGCAG TATTGCGTCA TCTCAAGCTA                               30

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GATCCGGCTG ACGCAATTCA AGCTA                                   25

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GATCCACAGT TGTGATTTCA CAACCTGACC AGA                          33

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GATCCGGCAC TATTGCGCAA TCTCAAGCTA                               30

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GATCCATATT AAGGACATGC CG                                      22

(2) INFORMATION FOR SEQ ID NO:18:

(i) SEQUENCE CHARACTERISTICS:
        (A) LENGTH: 1336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
ACGCTACAGA ACGGTCAAGA AATATAATGT GTGCAAAGAT GTCTGCTTAG GAAGACACGG      60
CGACGTCCGC CCCCAAGGGC AATCGGCACA ATGGCAACCT TTCATGATGT ATTCCTAGCT     120
ACGGCTATCT CGCTTCTCTA TTGGACGGAT TTATTTATCA CATAGAAGAC TCGTATACCA     180
AACTCTACGA TGGAGCTGGA CCTTTGGAGC GAAGATTTTC AACTGGCCAG GGAATGGGGG     240
CTGGAAATGC CAGTCGTCCA GACCGATGGC CAGTTCGGTG ACCTCAAATC AACCAGTCGT     300
CATGGTGGCG ACGAATCTCT AAGTTTGCAG CCCCAGGGCG CTACACTGAA GTTGGAACCC     360
TTTGAGGAAG ATGTCCTTGG TGCAGAGTGG ATGGAGTCGT CCGATCTCGG CTCTTTTCTG     420
GATGCTTTGG GTGACAACCA TGAGCGGCTG CATCCGTTCG AGTCAAACTT GCTCGAGTTC     480
ACTTCTCTGA TCACTCCTGA TGATTCGACG GTGTCAAAGG ACATTCTCAG CTCAACTCTT     540
CAGTTTCCAA CTCAACCAGT GAACATCCCT TTATATGCAA GTCATGGGGC CGAAGATTTC     600
TCTGCAGAGA CTGAGTTTGA GAACCACCTG TCGCCTCCAG ATTCTCCGGA GCAGGTAGCC     660
CCTGTCATAA ATCTAGAACC AGTTGAACTC ACTGCGAGCC ATATGACGGT GATCTCACCT     720
GATGGCTTGT TGGGTGGCAT GGAACTGGCT TCAGAAAGCT TAACATTTAC CGAACTAGAC     780
TTTGTGAACT TCAATGACAG TGCTGTTGGT TCAATTGGCG GTGCTGAAGA ACTTCTTGGC     840
TCCCCACTGT CAGTTGATGA TGTGGAAAGT ACAAATATCAT TTTCAGGTCC ATCGTCGCCA     900
GAAACCAGCC AGAGCAGCAT CATTGAATCA GTCCTGAAT TGTACAAAGT TATCTCTACC     960
TCGTCCATTG ATGCATCTAA GCGTTTCTCT CCATACTCTC GTTCCTCCAA GTCCAAGCAA    1020
TCTGTCAAGA CTTCAGACGC TAAGGCACCT CGTAAAACGA GGACACCGGC GCAGCCTGTG    1080
CCAGAACATG TCATCATGGA ACATTTGGAC AAAAAGGACA GAAAGAAGCT TCAGAACAAG    1140
AATGCTGCCA TTAGGTATAG GATGAAGAAG AAGGGGGAGG CTCAGGGCAT CAAAGGGGAG    1200
GAACAGGAAT TAGAAGAACT CAACACAAAG CTTAAGACTA AGGTCGATGA CTTGCAAAGA    1260
GAAATCAAGT ACATGAAAAA TTTAATGGAA GATGTTTGCA AGGCGAAAGG TATTCAGCTT    1320
AAATAGTGGG AAGGGT                                                    1336
```

(2) INFORMATION FOR SEQ ID NO:19:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Leu Asp Lys Lys Leu Lys Lys Met Glu Gln Asn Lys Thr Ala Ala Thr
1               5                   10                  15
Arg Tyr Arg Gln Lys Lys Arg Ala Glu Gln Glu Ala Leu Thr Gly Glu
            20                  25                  30
```

```
                             -continued

Cys Lys Glu Leu Glu Lys Lys Asn Glu Ala Leu Lys Glu Lys Ala Asp
        35                  40                  45

Ser Leu Ala Lys Glu Ile Gln Tyr Leu Lys Asp Leu Ile Glu Glu Val
    50                  55                  60

Arg Lys Ala Arg Gly Lys Lys Arg Val Pro
65                  70

(2) INFORMATION FOR SEQ ID NO:20:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Leu Asp Lys Lys Leu Lys Lys Met Glu Gln Asn Lys Thr Ala Ala Thr
1               5                  10                  15

Arg Tyr Arg Gln Lys Lys Arg Ala Glu Gln Glu Ala Leu Thr Gly Glu
            20                  25                  30

Cys Lys Glu Leu Glu Lys Lys Asn Glu Ala Leu Lys Glu Arg Ala Asp
        35                  40                  45

Ser Leu Ala Lys Glu Ile Gln Tyr Leu Lys Asp Leu Ile Glu Glu Val
    50                  55                  60

Arg Lys Ala Arg Gly Lys Lys Arg Val Pro
65                  70
```